「(12) United States Patent
Kim et al.

US010196475B2

(10) Patent No.: US 10,196,475 B2
(45) Date of Patent: *Feb. 5, 2019

(54) BLOCK COPOLYMER

(71) Applicant: LG Chem, Ltd., Seoul (KR)

(72) Inventors: Jung Keun Kim, Daejeon (KR); Jeong Kyu Lee, Daejeon (KR); Je Gwon Lee, Daejeon (KR); Mi Sook Lee, Daejeon (KR); No Jin Park, Daejeon (KR); Se Jin Ku, Daejeon (KR); Eun Young Choi, Daejeon (KR); Sung Joon Oh, Daejeon (KR); Sung Soo Yoon, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/173,671

(22) Filed: Jun. 5, 2016

(65) Prior Publication Data

US 2016/0280832 A1    Sep. 29, 2016

Related U.S. Application Data

(63) Continuation-in-part of application No. PCT/KR2014/012032, filed on Dec. 8, 2014.

(30) Foreign Application Priority Data

| Dec. 6, 2013 | (KR) | 10-2013-0151865 |
| Dec. 6, 2013 | (KR) | 10-2013-0151866 |
| Dec. 6, 2013 | (KR) | 10-2013-0151867 |
| Dec. 20, 2013 | (KR) | 10-2013-0159994 |
| Sep. 30, 2014 | (KR) | 10-2014-0131964 |
| Dec. 8, 2014 | (KR) | 10-2014-0175413 |

(51) Int. Cl.
| *C08F 293/00* | (2006.01) |
| *C07F 7/18* | (2006.01) |
| *C07C 43/215* | (2006.01) |
| *C07C 43/225* | (2006.01) |
| *C07C 217/84* | (2006.01) |
| *C07D 209/48* | (2006.01) |
| *C08F 12/20* | (2006.01) |
| *C08F 12/22* | (2006.01) |
| *C08F 12/26* | (2006.01) |
| *C08F 12/32* | (2006.01) |
| *C08F 212/14* | (2006.01) |
| *C08F 220/10* | (2006.01) |
| *C08F 220/30* | (2006.01) |
| *C08J 5/18* | (2006.01) |
| *G03F 7/00* | (2006.01) |
| *C08J 7/12* | (2006.01) |
| *C07C 35/48* | (2006.01) |
| *C08J 7/14* | (2006.01) |
| *C09D 153/00* | (2006.01) |
| *G03F 7/038* | (2006.01) |
| *G03F 7/039* | (2006.01) |
| *G03F 7/16* | (2006.01) |

(Continued)

(52) U.S. Cl.
CPC .......... *C08F 293/005* (2013.01); *C07C 35/48* (2013.01); *C07C 43/215* (2013.01); *C07C 43/225* (2013.01); *C07C 217/84* (2013.01); *C07D 209/48* (2013.01); *C07F 7/1804* (2013.01); *C08F 12/20* (2013.01); *C08F 12/22* (2013.01); *C08F 12/26* (2013.01); *C08F 12/32* (2013.01); *C08F 212/14* (2013.01); *C08F 220/10* (2013.01); *C08F 220/30* (2013.01); *C08J 5/18* (2013.01); *C08J 7/123* (2013.01); *C08J 7/14* (2013.01); *C09D 153/00* (2013.01); *G03F 7/0002* (2013.01); *G03F 7/038* (2013.01); *G03F 7/039* (2013.01); *G03F 7/162* (2013.01); *B81C 1/00428* (2013.01); *B81C 1/00531* (2013.01); *B81C 2201/0149* (2013.01); *B82Y 40/00* (2013.01); *C07C 2601/16* (2017.05); *C08F 2438/03* (2013.01); *C08J 2353/00* (2013.01)

(58) Field of Classification Search
CPC ........ C08F 212/14; C08F 12/32; C08F 12/26; C08F 12/22; C08F 12/20; C08L 53/00; C07D 209/48; C07C 43/214; C07C 217/84
See application file for complete search history.

(56) References Cited

U.S. PATENT DOCUMENTS

| 3,976,672 A | 8/1976 | Strunk et al. |
| 5,115,056 A | 5/1992 | Mueller et al. |
| 5,202,402 A | 4/1993 | Funaki et al. |

(Continued)

FOREIGN PATENT DOCUMENTS

| CN | 1333790 A | 1/2002 |
| CN | 1337974 A | 2/2002 |

(Continued)

OTHER PUBLICATIONS

Lee, electronic tranlsation of KR 1020160038705.*

(Continued)

*Primary Examiner* — Jeffrey C Mullis
(74) *Attorney, Agent, or Firm* — Lerner, David, Littenberg, Krumholz & Mentlik, LLP

(57) ABSTRACT

The present application provides the block copolymers and their application. The present application may provide the block copolymers that have excellent self assembling and phase separation properties and therefore that can be effectively used in various applications. The present application may also provide applications of the block copolymers.

16 Claims, 9 Drawing Sheets

(51) Int. Cl.
*B81C 1/00* (2006.01)
*B82Y 40/00* (2011.01)

(56) References Cited

U.S. PATENT DOCUMENTS

| | | | |
|---|---|---|---|
| 5,234,604 A | 8/1993 | Liao et al. | |
| 5,391,626 A | 2/1995 | Machida et al. | |
| 5,418,290 A | 5/1995 | Machida et al. | |
| 5,554,695 A | 9/1996 | Machida et al. | |
| 5,728,431 A | 3/1998 | Bergbreiter et al. | |
| 6,314,225 B1 | 11/2001 | Wang | |
| 6,531,547 B1 | 3/2003 | Visger et al. | |
| 6,546,282 B1 | 4/2003 | Inoue et al. | |
| 6,953,649 B2 | 10/2005 | Prat et al. | |
| 7,538,159 B2 | 5/2009 | Wang et al. | |
| 8,163,189 B2 | 4/2012 | Iyoda et al. | |
| 8,211,737 B2 | 7/2012 | Russell et al. | |
| 8,791,042 B2 | 7/2014 | Ronan et al. | |
| 9,495,991 B2 | 11/2016 | Han et al. | |
| 2003/0143343 A1 | 7/2003 | Kawabata et al. | |
| 2004/0049836 A1 | 3/2004 | Ashraf et al. | |
| 2004/0110856 A1 | 6/2004 | Young et al. | |
| 2004/0143032 A1 | 7/2004 | Auschra et al. | |
| 2004/0242787 A1 | 12/2004 | Chun et al. | |
| 2006/0166033 A1 | 7/2006 | Poetsch et al. | |
| 2007/0142559 A1 | 6/2007 | Wang et al. | |
| 2007/0166648 A1 | 7/2007 | Ponoth et al. | |
| 2007/0219338 A1 | 9/2007 | Takeda et al. | |
| 2008/0105854 A1 | 5/2008 | Huh et al. | |
| 2008/0193658 A1 | 8/2008 | Millward | |
| 2008/0286333 A1 | 11/2008 | Kangas et al. | |
| 2008/0311402 A1 | 12/2008 | Jung et al. | |
| 2009/0114108 A1 | 5/2009 | Oya et al. | |
| 2009/0240001 A1 | 9/2009 | Regner | |
| 2009/0253867 A1 | 10/2009 | Takahashi et al. | |
| 2009/0306295 A1 | 12/2009 | Mays et al. | |
| 2010/0086801 A1 | 4/2010 | Russell et al. | |
| 2010/0098876 A1 | 4/2010 | Hanson | |
| 2010/0102415 A1 | 4/2010 | Millward et al. | |
| 2010/0120985 A1 | 5/2010 | Konishi et al. | |
| 2010/0155988 A1 | 6/2010 | Keil et al. | |
| 2010/0206057 A1 | 8/2010 | Batchelder et al. | |
| 2010/0210742 A1 | 8/2010 | Iyoda et al. | |
| 2010/0216312 A1 | 8/2010 | Yamamoto et al. | |
| 2010/0266957 A1 | 10/2010 | Harada et al. | |
| 2010/0285276 A1 | 11/2010 | Kim et al. | |
| 2010/0286351 A1 | 11/2010 | Yoshida et al. | |
| 2010/0305230 A1 | 12/2010 | Li et al. | |
| 2011/0186544 A1 | 8/2011 | Endou et al. | |
| 2011/0253946 A1 | 10/2011 | Huh et al. | |
| 2011/0294070 A1 | 12/2011 | Hatakeyama et al. | |
| 2012/0052446 A1 | 3/2012 | Jaycox et al. | |
| 2012/0116024 A1 | 5/2012 | Lyoda et al. | |
| 2012/0214094 A1 | 8/2012 | Mikoshiba et al. | |
| 2013/0078576 A1 | 3/2013 | Wu et al. | |
| 2013/0183828 A1 | 7/2013 | Nakamura et al. | |
| 2013/0189504 A1 | 7/2013 | Nealey et al. | |
| 2013/0209693 A1 | 8/2013 | Vogel et al. | |
| 2013/0209755 A1 | 8/2013 | Hustad et al. | |
| 2013/0248488 A1 | 9/2013 | Han et al. | |
| 2013/0284698 A1 | 10/2013 | Ogihara | |
| 2013/0306594 A1 | 11/2013 | Hustad et al. | |
| 2014/0011916 A1 | 1/2014 | Lee et al. | |
| 2014/0127456 A1 | 5/2014 | Regner | |
| 2014/0141375 A1 | 5/2014 | Cho et al. | |
| 2014/0238954 A1 | 8/2014 | Matsumiya et al. | |
| 2014/0370442 A1 | 12/2014 | Ober et al. | |
| 2015/0064630 A1 | 3/2015 | Wuister et al. | |
| 2015/0085042 A1 | 3/2015 | Keoshkerian et al. | |
| 2015/0197663 A1 | 7/2015 | Mizutani et al. | |
| 2015/0228298 A1 | 8/2015 | Han et al. | |
| 2016/0204653 A1 | 7/2016 | Lee | |
| 2016/0257838 A1 | 9/2016 | Senzaki et al. | |
| 2016/0280823 A1 | 9/2016 | Kim et al. | |
| 2016/0280831 A1 | 9/2016 | Park et al. | |
| 2016/0280832 A1 | 9/2016 | Kim et al. | |
| 2016/0280833 A1 | 9/2016 | Lee et al. | |
| 2016/0280834 A1 | 9/2016 | Kim et al. | |
| 2016/0280835 A1 | 9/2016 | Lee et al. | |
| 2016/0304653 A1 | 10/2016 | Kim et al. | |
| 2016/0304654 A1 | 10/2016 | Lee et al. | |
| 2016/0304655 A1 | 10/2016 | Lee et al. | |
| 2016/0311958 A1 | 10/2016 | Kim et al. | |
| 2016/0311959 A1 | 10/2016 | Lee et al. | |
| 2016/0311960 A1 | 10/2016 | Lee et al. | |
| 2016/0333221 A1 | 11/2016 | Mumtaz et al. | |
| 2017/0008992 A1 | 1/2017 | Lee et al. | |
| 2017/0058071 A1 | 3/2017 | Lee et al. | |
| 2017/0210938 A1* | 7/2017 | Ku | C09D 153/00 |
| 2017/0219922 A1* | 8/2017 | Ku | G03F 1/24 250/372 |
| 2017/0226235 A1* | 8/2017 | Park | C08F 2/14 |
| 2017/0226258 A1* | 8/2017 | Lee | C08F 293/00 |
| 2017/0226260 A1* | 8/2017 | Lee | C08F 293/005 |
| 2017/0226261 A1* | 8/2017 | Lee | C08F 293/005 |
| 2017/0247492 A1 | 8/2017 | Choi et al. | |
| 2017/0306074 A1 | 10/2017 | Lee et al. | |
| 2017/0313869 A1 | 11/2017 | Lee et al. | |

FOREIGN PATENT DOCUMENTS

| | | |
|---|---|---|
| CN | 101215362 A | 7/2008 |
| CN | 101443371 A | 5/2009 |
| CN | 101492520 A | 7/2009 |
| CN | 101578232 A | 11/2009 |
| CN | 101688047 A | 3/2010 |
| CN | 101799626 A | 8/2010 |
| CN | 101977839 A | 2/2011 |
| CN | 102172491 A | 9/2011 |
| CN | 102439076 A | 5/2012 |
| CN | 102967918 A | 3/2013 |
| CN | 103025827 A | 4/2013 |
| CN | 103180783 A | 6/2013 |
| CN | 103289285 A | 9/2013 |
| CN | 103562245 A | 2/2014 |
| CN | 105899556 A | 8/2016 |
| CN | 105899557 A | 8/2016 |
| CN | 105899559 A | 8/2016 |
| CN | 105899560 A | 8/2016 |
| CN | 105934454 A | 9/2016 |
| CN | 105934456 A | 9/2016 |
| CN | 105960422 A | 9/2016 |
| CN | 105980342 A | 9/2016 |
| CN | 106459326 A | 2/2017 |
| EP | 1141056 B1 | 8/2010 |
| EP | 2781550 A1 | 9/2014 |
| EP | 3078654 A1 | 10/2016 |
| EP | 3078691 B1 | 10/2016 |
| EP | 3078692 A1 | 10/2016 |
| EP | 3078694 A1 | 10/2016 |
| EP | 3203497 A1 | 8/2017 |
| EP | 3214102 A1 | 9/2017 |
| EP | 3225641 A1 | 10/2017 |
| GB | 898065 A | 6/1962 |
| JP | 01260360 A | 10/1989 |
| JP | H01-260360 A | 10/1989 |
| JP | H5320281 A | 12/1993 |
| JP | H0665333 A | 3/1994 |
| JP | H10237143 A | 9/1998 |
| JP | H10245427 A | 9/1998 |
| JP | H1143523 A | 2/1999 |
| JP | 2000053734 A | 2/2000 |
| JP | 2000281737 A | 10/2000 |
| JP | 2000285751 A | 10/2000 |
| JP | 3121116 B2 | 12/2000 |
| JP | 2001513125 A | 8/2001 |
| JP | 2001294617 A | 10/2001 |
| JP | 2002145973 A | 5/2002 |
| JP | 2003536105 A | 12/2003 |
| JP | 2004026688 A | 1/2004 |
| JP | 2004323773 A | 11/2004 |
| JP | 2005015508 A | 1/2005 |
| JP | 2005097442 A | 4/2005 |
| JP | 2005148205 A | 6/2005 |

(56) References Cited

FOREIGN PATENT DOCUMENTS

| | | |
|---|---|---|
| JP | 2005530030 A | 10/2005 |
| JP | 2005531618 A | 10/2005 |
| JP | 2007070453 A | 3/2007 |
| JP | 2007077292 A | 3/2007 |
| JP | 2007246600 A | 9/2007 |
| JP | 200855579 A | 3/2008 |
| JP | 2009057519 A | 3/2009 |
| JP | 200986354 A | 4/2009 |
| JP | 2009203439 A | 9/2009 |
| JP | 2010507803 A | 3/2010 |
| JP | 2010115832 A | 5/2010 |
| JP | 2010145158 A | 7/2010 |
| JP | 2010202723 A | 9/2010 |
| JP | 2010275349 A | 12/2010 |
| JP | 4625901 B2 | 2/2011 |
| JP | 2012001787 A | 1/2012 |
| JP | 2012012577 A | 1/2012 |
| JP | 2012093699 A | 5/2012 |
| JP | 2012174984 A | 9/2012 |
| JP | 201368882 A | 4/2013 |
| JP | 2013512323 A | 4/2013 |
| JP | 2013514449 A | 4/2013 |
| JP | 2013121430 A | 6/2013 |
| JP | 2013219334 A | 10/2013 |
| JP | 2013232501 A | 11/2013 |
| JP | 201412807 A | 1/2014 |
| JP | 2014070154 A | 4/2014 |
| JP | 2014102503 A | 6/2014 |
| JP | 2014162504 A | 9/2014 |
| JP | 2015000896 A | 1/2015 |
| JP | 2016539239 A | 12/2016 |
| JP | 2016540863 A | 12/2016 |
| JP | 2017502116 A | 1/2017 |
| JP | 2017505356 A | 2/2017 |
| JP | 2017530236 A | 10/2017 |
| JP | 2017530238 A | 10/2017 |
| JP | 2017533302 A | 11/2017 |
| KR | 20010101356 | 11/2001 |
| KR | 100622353 B1 | 9/2006 |
| KR | 20090015742 A | 2/2009 |
| KR | 100935863 B1 | 1/2010 |
| KR | 20100033962 A | 3/2010 |
| KR | 20100070380 A | 6/2010 |
| KR | 20100123920 A | 11/2010 |
| KR | 20110018678 A | 2/2011 |
| KR | 20110086834 A | 8/2011 |
| KR | 20110097707 A | 8/2011 |
| KR | 20110102998 A | 9/2011 |
| KR | 20110112501 A | 10/2011 |
| KR | 101102680 B1 | 1/2012 |
| KR | 20120119998 A | 11/2012 |
| KR | 20130094264 A | 8/2013 |
| KR | 20130113596 A | 10/2013 |
| KR | 20130128346 A | 11/2013 |
| KR | 20140063790 A | 5/2014 |
| KR | 20150066488 A | 6/2015 |
| KR | 20150067065 A | 6/2015 |
| KR | 20150067070 A | 6/2015 |
| KR | 1020150067069 A | 6/2015 |
| KR | 20160038705 A | 4/2016 |
| TW | 201323461 A | 6/2013 |
| TW | 201428046 A | 7/2014 |
| TW | 201536823 A | 10/2015 |
| TW | 201538548 A | 10/2015 |
| WO | 9837136 A1 | 8/1998 |
| WO | 2007055371 A1 | 5/2007 |
| WO | 2012144735 A2 | 10/2012 |
| WO | 2013069544 A1 | 5/2013 |
| WO | 2013120051 A1 | 8/2013 |
| WO | 2013158527 A1 | 10/2013 |
| WO | 2014050905 A1 | 4/2014 |
| WO | 2014090178 A1 | 6/2014 |
| WO | 2014124795 A1 | 8/2014 |
| WO | 2015084121 A1 | 6/2015 |
| WO | 2015084122 A1 | 6/2015 |
| WO | 2015084123 A1 | 6/2015 |
| WO | 2015084124 A1 | 6/2015 |
| WO | 2015084125 A1 | 6/2015 |
| WO | 2015084126 A1 | 6/2015 |
| WO | 2015084127 A1 | 6/2015 |
| WO | 2015087005 A1 | 6/2015 |
| WO | 2016052994 A1 | 4/2016 |
| WO | 2016052999 A1 | 4/2016 |
| WO | 2016053005 A1 | 4/2016 |
| WO | 2016053007 A1 | 4/2016 |

OTHER PUBLICATIONS

Riedel et al., Synthesis, post-modification and self-assembled thin films of pentafluorostyrene containing block copolymers, European Polymer Journal 47 (2011) 675-684.*
Electronic translation of Eiji et al., JP 2009-203439 (Sep. 2009).*
Hua et al. Temperature-induced phase-transitions of methoxyoligo(oxyethylene) styrene-based block copolymers in aqueous solution, Soft Matter, 2013, 9, 8897.
Khazimullis et al. "Gel formation in a mixture of a block copolymer and a nematic liquid crystal", Physical Review E 84, 021710 (2011).
Tenneti et al. "Competition between liquid crystallinity and block copolymer self-assembly in core-shell rod-coil block copolymers", Soft Matter, 2008, 4, 458-461 (2008).
Tenneti et al. Hierarchical Nanostructures of Mesogen Jacketed Bent-Core Liquid Crystalline Block Copolymers, Proceedings Published 2007 by the American Chemical Society.
International Search Report from PCT/KR2015/010338 dated Jan. 14, 2016.
U.S. Appl. No. 15/515,821, filed Mar. 30, 2017.
U.S. Appl. No. 15/514,929, filed Mar. 28, 2017.
U.S. Appl. No. 15/514,939, filed Mar. 28, 2017.
U.S. Appl. No. 15/514,959, filed Mar. 28, 2017.
U.S. Appl. No. 15/514,967, filed Mar. 28, 2017.
U.S. Appl. No. 15/515,290, filed Mar. 29, 2017.
U.S. Appl. No. 15/515,812, filed Mar. 30, 2017.
U.S. Appl. No. 15/515,818, filed Mar. 30, 2017.
U.S. Appl. No. 15/515,293, filed Mar. 29, 2017.
U.S. Appl. No. 15/515,432, filed Mar. 29, 2017.
International Search Report from PCT/KR2015/010313, dated Nov. 23, 2015.
International Search Report from PCT/KR2015/010335 dated Jan. 13, 2016.
IPO Search Report from Taiwan Application No. 104132186, dated Aug. 18, 2016.
International Search Report from PCT/KR2015/010334, dated Jan. 13, 2016.
International Search Report from PCT/KR2015/010323, dated Jan. 13, 2016.
International Search Report from PCT/KR2015/010320, dated Jan. 13, 2016.
International Search Report from PCT/KR2015/010322, dated Jan. 13, 2016.
International Search Report from PCT/KR2015/010327, dated Jan. 12, 2016.
International Search Report from PCT/KR2015/010330 dated Jan. 11, 2016.
Park et al., "Block Copolymer Lithography: Periodic Arrays of ~10 11 Holes in 1 Square Centimeter", Science 276, p. 1401-1404, May 30, 1997.
International Search Report from PCT/KR2015/010332 dated Jan. 13, 2016.
International Search Report from PCT/KR2014/012023, dated Mar. 10, 2015.
IPO Search Report from Taiwan Application No. 103142955, dated Jan. 15, 2016.
International Search Report from PCT/KR2014/012024, dated Mar. 17, 2015.
IPO Search Report from Taiwan Application No. 103142805, dated Dec. 11, 2015.
International Search Report from PCT/KR2014/012025, dated Mar. 17, 2015.

(56) References Cited

OTHER PUBLICATIONS

IPO Search Report from Taiwan Application No. 103142784, dated Jan. 27, 2016.
International Search Report from PCT/KR2014/012026, dated Mar. 17, 2015.
International Search Report from PCT/KR2014/012027, dated Mar. 17, 2015.
IPO Search Report from Tawain Application No. 103142782, dated Dec. 11, 2015.
International Search Report from PCT/KR2014/012028, dated Mar. 17, 2015.
IPO Search Report from Taiwan Application No. 103142798, dated Dec. 16, 2015.
International Search Report from PCT/KR2014/012029, dated Mar. 17, 2015.
IPO Search Report from Taiwan Application No. 103142780, dated Dec. 15, 2015.
International Search Report from PCT/KR2014/012030, dated Mar. 17, 2015.
IPO Search Report from Taiwan Application No. 103142790, dated Dec. 15, 2015.
International Search Report from PCT/KR2014/012031, dated Feb. 12, 2015.
IPO Search Report from Taiwan Application No. 103142956 dated Jan. 20, 2016.
International Search Report from PCT/KR2014/012032, dated Feb. 12, 2015.
IPO Search Report from Taiwan Application No. 103142777, dated Dec. 15, 2015.
International Search Report from PCT/KR2014/012033, dated Feb. 12, 2015.
IPO Search Report from Taiwan Application No. 103142963, dated Dec. 10, 2015.
International Search Report from PCT/KR2014/012034, dated Feb. 12, 2015.
IPO Search Report from Taiwan Application No. 103142745, dated Dec. 14, 2015.
International Search Report from PCT/KR2014/012035, dated Feb. 12, 2015.
Akira, Isamu, et al., "Self-Assembly of Amphiphilic Block Copolymers Containing Poly(n-octadecyl acrylate) Block in Aqueous Solution." IOP Conference Series: Materials Science and Engineering, 2010, vol. 14, No. 1, pp. 1-8.
IPO Search Report from Taiwan Application No. 103142794, dated Dec. 15, 2015.
IPO Search Report from Taiwan Application No. 103142786, dated Jan. 11, 2016.
International Search Report from PCT/KR2014/012036, dated Mar. 17, 2015.
U.S. Appl. No. 15/101,794, filed Jun. 3, 2016.
U.S. Appl. No. 15/101,827, filed Jun. 3, 2016.
U.S. Appl. No. 15/101,915, filed Jun. 5, 2016.
U.S. Appl. No. 15/101,812, filed Jun. 3, 2016.
U.S. Appl. No. 15/102,089, filed Jun. 6, 2016.
U.S. Appl. No. 15/102,112, filed Jun. 6, 2016.
U.S. Appl. No. 15/102,139, filed Jun. 6, 2016.
U.S. Appl. No. 15/102,149, filed Jun. 6, 2016.
U.S. Appl. No. 15/102,156, filed Jun. 6, 2016.
U.S. Appl. No. 15/173,670, filed Jun. 5, 2016.
U.S. Appl. No. 15/173,673, filed Jun. 5, 2016.
U.S. Appl. No. 15/173,674, filed Jun. 5, 2016.
U.S. Appl. No. 15/173,676, filed Jun. 5, 2016.
Database CA [Online] Chemical Abstracts Service Ohi0 US; Zou, Yue: "Fluorosurfactant capable of preventing unevenness in photoresist coating and its preparation by anionic polymerization", XP002771143 retrieved from STN Database accession No. 2011:1148166 * abstract * & CN 102 172 491 A (Jiangsu Johnny Material Technology Co Ltd) Sep. 7, 011 (Sep. 7, 2011) Columbus, No. 2011:1148166.

European Search Report for Application No. EP14867501 dated Jul. 14, 2017.
Kago K et al: "X-ray reflectivity of polymer assembly at air-water interface" Supramolecular Science Butterworth-Heinemann Oxford GB vol. 5 No. 3-4, Jul. 1, 1998 (Jul. 1, 1998)pp. 349-355 XP027388373 ISSN: 0968-5677 [retrieved on Jul. 1, 1998]* abstract *.
Lutz Funk et al: "Novel Amphiphilic Styrene-Based Block Copolymers for Induced Surface Reconstruction". Macromolecular Chemistry and Physics., vol. 209, No. 1, Jan. 4, 2008 (Jan. 4, 2008), XP055382259 DE ISSN: 1022-1352 D0I: 10.1002/macp. 200700312 * scheme 1, monomers M1, M4 table 2*.
Mori H et al: "Synthesis and Surface Characterization of Hydrophilic-Hydrophobic Block Copolymers Containing Poly(2, 3-Dihydroxypropyl Methacrylate)" Macromolecules American Chemical Society US vol. 27 No. 15 Jul. 18, 1994 (Jul. 18, 1994) pp. 4093-4100 XP000456650 ISSN: 0024-9297 D01: 10.1021/MA00093A010 * abstract *.
CN Search Report for Application No. 201480071920.0 dated Aug. 2, 2017.
CN Search Report for Application No. CN201480072884.X dated Aug. 3, 2017.
CN Search Report for Application No. CN2014800740447 dated Aug. 1, 2017.
Extended European Search Report for Application No. EP14867273 dated Aug. 10, 2017.
Mariana Beija et al: " Fluorescence Anisotropy of Hydrophobic Probes in poly(N-decylacrylamide) block-poly( N,N-diethylacrylamide) Block Copolymer Aqueous Solutions: Evidence of Premicellar Aggregates" Journal of Physical Chemistry Part B: Condensed Matter, Materials, Surfaces, Interfaces & Bi0physical, vol. 114, No. 31, Aug. 12, 2010 (Aug. 12, 2010), 9977-9986, XP055394763, US ISSN: 1520-6106, D0I: 10.1021/jp101613y * abstract ** Scheme 1, PDcA11-block-PDEA295; p. 9978 *.
Anonymous., "Solid surface energy data (SFE) for common polymers", surface-tension.de, Feb. 2017, Retreived from the Internet: URL:http://www.surface-tension.de/solid-surface-energy.htm, XP002775246.
Cummins et al., "Solvothermal Vapor Annealing of Lamellar Poly-(styrene)-block-poly(D,L-lactide) Block Copolymer Thin Films for Directed Self-Assembly Application", ACS Applied Materials & Interfaces, Mar. 2016, vol. 8, No. 12, pp. 8295-8304, XP055419698.
Extended European Search Report for Application No. EP14867808.9 dated Nov. 10, 2017.
Extended European Search Report for Application No. EP14868022.6 dated Nov. 6, 2017.
Extended European Search Report for Application No. EP14868320.4 dated Nov. 20, 2017.
Extended European Search Report for Application No. EP14868480.6 dated Nov. 2, 2017.
Hvilsted et al., "Novel Fluorinated Polymer Materials Based on 2,3,5,6-Tetrafluoro-4-methoxyystyrene" In: "Advances in Controlled/ Living Radical Polymerization", American Chemical Society, Jun. 26, 2003, vol. 854, pp. 236-249, XP055421064.
Mahajan et al., "Synthesis and Characterization of Amphiphilic Poly(ethylene oxide)-block-poly(hexylmethacrylate Copolymers", Macromolecular Chemistry and Physics, Wiley-Vch Verlag, Weinheim, DE, Jan. 2003, vol. 204, pp. 1047-1055, XP003030406.
Pochan et al., "Morphologies of microphase-seperated conformationally asymmetric diblock copolymers", Journal of Jolymer Science Part B: Polymer Physics, Nov. 2017, vol. 35, No. 16, pp. 2629-2643, XP055417266.
Zhuang et al., "Synthesis of A-B type block copolymers using 1-phenylethyl dithiobenzoate as Reversible Addition-Fragmentation Chain Transfer agent", Database CA [online], Chemical Abstracts Service, Columbus, OH, XP002775247.
Yoshida, E. et al. Polymer Journal vol. 31 (5) pp. 429-434 (1999).
C.M. Bates et al., "Polymeric Cross-Linked Surface Treatments for Controlling Block Copolymer Orientation in Thin Films", Langmuir Article, American Chemical Society, Jan. 7, 2011, vol. 27, No. 5, pp. 1-7.
Extended European Search Report including Written Opinion for Application No. EP15845665.7 dated Jun. 27, 2018.

(56) References Cited

OTHER PUBLICATIONS

Katja Nilles et al., "RAFT Polymerization of Activated 4-Vinylbenzoates"., Journal of Polymer Science: Part A: Polymer Chemistry, Jan. 1, 2009, vol. 47, pp. 1696-1705.
Truelsen et al., "Synthesis by ATRP of triblock copolymers with densely grafted styrenic end blocks from a polyisobutylene macroinitiator", Marcomol. Rapid. Commun., Jul. 2, 1999, vol. 21, No. 2, pp. 1-5.
Chinese Search Report for Application No. 201480072759.9 dated Jan. 24, 2018.
Chinese Search Report for Application No. 2014800727599 dated Jan. 8, 2018.
Chinese Search Report for Application No. 2014800741401 dated Mar. 9, 2018.
Chinese Search Report for Application No. 201480074156.2 dated Apr. 3, 2018.
CN Search Report for Application No. 201480071920.0 dated Aug. 2, 2017, completed Jul. 25, 2017.
CN Search Report for Application No. CN201480072884.X dated Aug. 3, 2017. completed Jul. 26, 2017.
CN Search Report for Application No. CN2014800740447 dated Aug. 1, 2017, completed Jul. 10, 2017.
Palacios et al., Constructing Robust and Functional Micropatterns on Polystyrene Surfaces by Using Deep UV Irradiation, American Chemical Society, Langmuir, 29(8) pp. 2756-2763, Feb. 2013.
Supplementary European Search Report for EP15847157 dated Mar. 21, 2018.
Chakrabarty, et al., "Tailor-Made Polyfluoroacrylate and its Block Copolymer by RAFT Polymerization in Miniemulsion; Improved Hydrophobicity in the Core-Shell Block Copolymer", Journal of Colloid and Interface Science, vol. 408, Oct. 2013, pp. 66-74.
Gregory, et al., "Complex Polymer Architectures via RAFT Polymerization: From Fundamental Process to Extending the Scope Using Click Chemistry and Nature's Building Blocks", Progress in Polymer Science, vol. 37, No. 1, Jan. 2012, pp. 38-105.
Chinese Search Report for CN Application No. 201480071920.0, dated May 4, 2018.
Chinese Search Report for CN Application No. 201480072800.2, dated Apr. 10, 2018.
Chinese Search Report for CN Application No. 201480074045.1, dated Apr. 11, 2018.
Extended European Seach Report including Written Opinion for EP Application No. 15847574.9, dated May 3, 2018.
Extended European Search Report including Written Opinion for EP Application No. 15845928.9, dated May 2, 2018.
Extended European Search Report including Written Opinion for EP Application No. 15847598.8, dated May 11, 2018.
Extended European Search Report including Written Opinion for EP15845720.0 dated May 4, 2018.
Extended European Search Report with Written Opinion for EP15846832.2 dated May 3, 2018.
Funk, L. et al., "Novel Amphiphilic Styrene-Based Block Copolymers for Induced Surface Reconstruction," Macromolecular Chemistry and Physics, vol. 209, No. 1, Jan. 4, 2008, pp. 52-63, XP055382259, DE, ISSN: 1022-1352, DOI: 10.1002/macp.200700312.
Haeng-Dong Koh et al., "Location-controlled parallel and vertical orientation by dewetting-induced block copolymer lirected self-assembly," Journal of Materials Chemistry C: Materials for Optical and Electronic Devices, vol. 1, No. 25, Jan. 1, 2013, pp. 4020-4024 XP055469744.
Ma J et al, "Synthesis and Solution-State Assembly or Buld State Thiol-ene Crosslinking of Pyrrolidinone- and Alkene-Functionalized Amphiphilic Block Fluorocopoplymers: From Functional Nanoparticles to Anti-Fouling Coatings", Australian Journal of Chemistry: An International Journal for Chemical Sci, Jan. 1, 2010, pp. 1159-1163, vol. 63, No. 8,C S I R O Publishing, Australia.
Mori H. et al., "Synthesis and Surface Characterization of Hydrophilic-Hydrophobic Block Copolymers Containing Poly(2,3-dihydroxypropyl methacrylate)," Macromolecules, American Chemical Society, US, vol. 27, No. 15, Jul. 18, 1994, pp. 4093-9297; XP000456650, DOI: 10.2021/MA00093A010.
Segalman R.A. et al., "Graphoepitaxy of Spherical Domain Block Copolymer Films," Advanced Materials, Wiley-VCH Verlag GmbH & Co. KGAA, DE, vol. 13, No. 15, Aug. 3, 2001, pp. 1152-1155; XP001129643, ISSN: 0935-9648, DOI: 10.1002/1521-4095(200108)13:15<1152: AID-A DMA1152>3.0.CO; 2-5.
Beng H. Tan et al, "Synthesis and Self-Assembly of pH-Responsive Amphiphilic Poly (dimethylaminoethylmethacrylate)-block-Poly(pentafluorostyrene) Block Copolymer in Aqueous Solution", Macromolecular Rapid Communications, 2009, vol. 30, pp. 1002-1008.
Chinese Search Report for CN Application No. 201480074044.7 dated Jun. 7, 2018.
Frank S. Bates et al., "Block Copolymer Thermodyanmics: Theory and Experiment", Annu. Rev. Phys. Chem., 1990, vol. 41, pp. 525-557.
G. R. Strobl, "The Physics of Polymers: Concepts for Understanding Their Structures and Behavior", Springer Abstract Only), (2007).
S. Chavda et al., "Synthesis of stimuli responsive PEG47-b-PAA126-b-PSt32 triblock copolymer and its self-assembly in aqueous solutions", European Polymer Journal, Sep. 2012, vol. 49, pp. 209-216.
Sachin Borkar et al., "New Highly Fluorinated Styrene-Based Materials with Low Surface Energy Prepared by ATRP", Macromolecules, Jan. 2004, vol. 37, pp. 788-794.

* cited by examiner

BLOCK COPOLYMER

CROSS-REFERENCE TO RELATED APPLICATION

This application is a continuation-in-part of International Application No. PCT/KR2014/012032 filed on Dec. 8, 2014, which claims priority from Korean Patent Application Nos. 10-2013-0151866, filed Dec. 6, 2013, Korean Patent Application No. 10-2013-0151865, filed Dec. 6, 2013, Korean Patent Application No. 10-2013-0151867, filed Dec. 6, 2013, Korean Patent Application No. 10-2013-0159994, filed Dec. 20, 2013, Korean Patent Application No. 10-2014-0131964, filed Sep. 30, 2014 and Korean Patent Application No. 10-2014-0175413, filed Dec. 8, 2014.

TECHNICAL FIELD

The present application relates to block copolymers and their application.

BACKGROUND

Block copolymers have molecular structures in which polymer subunits having chemically different structures from each other are linked by covalent bonds. Block copolymers are capable of forming periodically aligned structure such as the sphere, the cylinder or the lamella through phase separations. Sizes of domains of the structures formed by the self assemblies of block copolymers may be adjusted in a wide range, and various shapes of structures can be prepared. Therefore, they can be utilized in pattern-forming methods by lithography, various magnetic recording mediae or next generation nano devices such as metal dots, quantum dots or nano lines, high density magnetic storage mediae, and the like.

DESCRIPTION

Technical Object

The present application provides a block copolymer, a polymer layer including the block copolymer, a method for forming the polymer layer and a pattern-forming method.

Technical Solution

The block copolymer may include a first block and a second block that is different from the first block. The block copolymer may be a diblock copolymer that includes only the above first and second blocks or may be a block copolymer that includes an additional block other than the first and second blocks.

The block copolymers may be phase-separated, since they comprise the two or more polymeric chains linked to each other via covalent bonds. In the present application, since the block copolymer satisfies at least one parameters as described below, the phase-separation can be very effectively occurred, and therefore it can form a nano-scaled structure by a microphase separation. According to the present application, by controlling sizes such as molecular weights or relative ratios between blocks, Sizes or shapes of the nano structure can be freely adjusted. By the above, the block copolymer can freely form various sizes of phase-separated structure such as the sphere, the cylinder, the gyroid, the lamella and the reversed structure and the like. The present inventors have found that, if block copolymers satisfy at least one parameter among ones described below, the self assembling properties and the phase separation properties as described above are largely improved. It is confirmed that it is possible to make the block copolymer to show a vertically aligning property by making the block copolymer to satisfy an appropriate parameter. The term "vertically aligning property" as used herein may refer to aligning property of the block copolymer and may refer to a case where the nano scaled structure formed by the block copolymer is aligned vertically to a direction of a substrate. Techniques controlling an aligning of a self assembled structure of a block copolymer to be vertical or parallel with respect to various substrates are a big part of practical application of a block copolymer. Conventionally, the aligning direction of the nano scaled structure in a layer of a block copolymer depends on what block among blocks forming the block copolymer is exposed to a surface or an air. Generally, since lots of substrates are polar and the air is non-polar, a block having more polarity than the other block in the block copolymer wets on the substrate and a block having less polarity than the other block in the block copolymer wets with respect to the interface between the air. Many techniques are proposed in order for blocks of a block copolymer having properties different from each other to wet simultaneously toward the substrate, and a most typical method is to control the aligning by preparing the neutral surface. However, in one embodiment, by controlling the parameters below, the block copolymer may be vertically aligned with respect to substrates, to which conventionally known treatment for accomplishing the vertical alignment including the neutral surface treatment is not performed. For example, block copolymers according to one embodiment of the present application can show the vertical aligning property on both of hydrophobic surfaces and hydrophilic surfaces, to which any pre-treatment is not performed. Further, in an additional embodiment, the vertical alignment may be accomplished with respect to a large area in a short time by a thermal annealing.

The block copolymer may exhibit at least one peak within a predetermined range of the scattering vector (q) in the XRD (X ray diffraction) analysis.

In one embodiment, when the XRD is performed, the block copolymer may show at least one peak within a range from $0.5 \text{ nm}^{-1}$ to $10 \text{ nm}^{-1}$ of the scattering vectors (the q values). In other embodiment, the range of the scattering vectors (the q values) within which the at least one peak is observed may be from $0.7 \text{ nm}^{-1}$ or more, $0.9 \text{ nm}^{-1}$ or more, $1.1 \text{ nm}^{-1}$ or more, $1.3 \text{ nm}^{-1}$ or more or $1.5 \text{ nm}^{-1}$ or more. In other embodiment, the range of the scattering vectors (the q values) within which the at least one peak is observed may be from $9 \text{ nm}^{-1}$ or less, $8 \text{ nm}^{-1}$ or less, $7 \text{ nm}^{-1}$ or less, $6 \text{ nm}^{-1}$ or less, $5 \text{ nm}^{-1}$ or less, $4 \text{ nm}^{-1}$ or less, $3.5 \text{ nm}^{-1}$ or less or $3 \text{ nm}^{-1}$ or less.

The FWHM (full width at half maximum) of the peak observed within the above range of the scattering vectors (q) may be from $0.2 \text{ nm}^{-1}$ to $0.9 \text{ nm}^{-1}$. In another embodiment, the FWHM may be $0.25 \text{ nm}^{-1}$ or more, $0.3 \text{ nm}^{-1}$ or more or $0.4 \text{ nm}^{-1}$ or more. The FWHM may be, in another embodiment, $0.85 \text{ nm}^{-1}$ or less, $0.8 \text{ nm}^{-1}$ or less or $0.75 \text{ nm}^{-1}$ or less.

The term "FWHM (full width at half maximum)" as used herein may refer to a width (difference between scattering vectors (q's)) of a peak showing an intensity half times as large as the maximum intensity.

In the XRD analysis, the scattering vector (q) and the FWHM are values by a numerical analysis, in which the least square technique is used, with respect to results of the XRD analysis described below. In the above method, the Gaussian fitting is performed with respect to a profile of peaks in the XRD pattern under a state where a position at which a XRD diffraction pattern has a lowest intensity becomes a baseline and the lowest intensity is converted to zero, and then the scattering vector (q) and the FWHM are obtained from the result of the Gaussian fitting. The R square of the Gaussian fitting is at least 0.9 or more, 0.92 or more, 0.94 or more or 0.96 or more. The method obtaining the above information from the XRD analysis is known, and, for example, a numerical value analysis program such as the origin may be used.

The block copolymer showing the peak having the above FWHM within the above range of scattering vectors (q's) may include a crystalline portion suitable for the self assembling. The block copolymer showing the peak having the above FWHM within the above range of scattering vectors (q's) may show an excellent self assembling property.

The XRD analysis may be performed by passing X-ray through a sample of the block copolymer and then measuring a scattering intensity according to scattering vector. The XRD analysis may be performed with respect to a block copolymer without any specific pre-treatment, and, for example, it may be performed by drying the block copolymer under an appropriate condition and then passing X ray through it. As the X ray, X ray, a vertical size of which is 0.023 mm and a horizontal size of which is 0.3 mm can be used. By using a measuring device (for example, 2D marCCD), a 2D diffraction pattern scattered from the sample is obtained as an image, and then the above fitting is performed with respect to the obtained diffraction pattern so as to obtain the scattering vector and the FWHM, and the like.

The above parameter may be realized by, for example, controlling the structure of the block copolymer.

For example, the block copolymer satisfying the above parameter may include a side chain in the first block or the second block. Hereinafter, for the sake of convenient explanation, the block comprising the side chain may be referred to as the first block.

The term "chain-forming atoms" as used herein refers to atoms forming the side chain linked to the block copolymer and atoms forming a linear structure of the side chain. The side chain may have a linear or branched structure; however the number of the chain-forming atoms is calculated only by the number of atoms forming the longest linear chain. Therefore, other atoms such as, in a case where the chain-forming atom is the carbon atom, the hydrogen atom that is linked to the carbon atom and the like are not calculated as the number of the chain-forming atoms. Further, in case of the branched chain, the number of the chain-forming atoms is the number of atoms forming the longest chain. For example, the chain is n-pentyl, all of the chain-forming atoms are carbon atoms and the number thereof is 5. If the chain is 2-methylpentyl, all of the chain-forming atoms are also carbon atoms and the number thereof is 5. The chain-forming atoms may be the carbon, the oxygen, the sulfur or the nitrogen, and the like and appropriate chain-forming atoms may be the carbon, the oxygen or the nitrogen; or the carbon or the oxygen. The number of the chain-forming atoms may be 8 or more, 9 or more, 10 or more, 11 or more; or 12 or more. The number of the chain-forming atoms may be 30 or less, 25 or less, 20 or less or 16 or less.

In another embodiment, one or both of the first block and the second block may include at least aromatic structure in the block copolymer satisfying the above parameter. Both of the first block and the second block may include the aromatic structure(s) and, in this case, the aromatic structure in the first block may be the same as or different from the aromatic structure in the second block. Further, at least one block among the first and second blocks of the block copolymer satisfying parameters described in this document may include the side chain or at least one halogen atom as described below, and such a side chain or at least one halogen atom may be substituted with the aromatic structure. The block copolymer may include two or more blocks.

As described, the first block and/or the second block of the block copolymer may include the aromatic structure(s). Such an aromatic structure may be included in one of or both of the first block and the second block. In case where both of the blocks include the aromatic structures, the aromatic structure in the first block may be the same as or different from the aromatic structure in the second block.

The term "aromatic structure" as used herein may refer to an aryl or arylene group, and may refer to a monovalent or a bivalent substituent derived from a compound including one benzene ring structure or a structure, in which at least two benzene rings are linked with sharing one or two carbon atoms or by an optional linker, or a derivative of the compound. The aryl or arylene group may be, unless defined otherwise, an aryl group having 6 to 30, 6 to 25, 6 to 21, 6 to 18, or 6 to 13 carbon atoms. As the aryl or arylene group, a monovalent or a bivalent substituent derived from benzene, naphthalene, azobenzene, anthracene, phenanthrene, tetracene, pyrene, benzopyrene, and the like may be illustrated.

The aromatic structure may be a structure included in a main chain of the block or may be a structure linked to the main chain of the block as a side chain. For example, appropriate adjustment of the aromatic structure that may be included in each block may realize controlling of the parameters.

For example, in order to control the parameter, the chain having 8 or more chain-forming atoms may be linked, as a side chain, to first block of the block copolymer. In this document, the term "side chain" and the term "chain" may indicate to the same object. In case where the first block includes the aromatic structure, the chain may be linked to the aromatic structure.

The side chain may be a chain linked to a main chain of polymer. As described, the side chain may be a chain including 8 or more, 9 or more, 10 or more, 11 or more or 12 or more chain-forming atoms. The number of the chain-forming atoms may be 30 or less, 25 or less, 20 or less or 16 or less. The chain-forming atom may be carbon, oxygen, nitrogen or sulfur, or appropriately carbon or oxygen.

The side chain may be a hydrocarbon chain such as an alkyl group, an alkenyl group or an alkynyl group. At least one carbon atom in the hydrocarbon chain may be replaced with the sulfur atom, the oxygen atom or the nitrogen atom.

In case where the side chain is linked to the aromatic structure, the chain may be directly linked to the aromatic structure or may be linked to the aromatic structure via a linker. The linker may be an oxygen atom, a sulfur atom, $-NR_1-$, $-S(=O)_2-$, a carbonyl group, an alkylene group, an alkenylene group, an alkynylene group, $-C(=O)-X_1-$ or $-X_1-C(=O)-$. In the above, the $R_1$ may be hydrogen, an alkyl group, an alkenyl group, an alkynyl group, an alkoxy group or an aryl group and the $X_1$ may be a single bond, an oxygen atom, a sulfur atom, $-NR_2-$, $-S(=O)_2-$, an alkylene group, an alkenylene group or alkynylene group, and the $R_2$ may be hydrogen, an alkyl group, an alkenyl group, an alkynyl group, an alkoxy group or an aryl group. An appropriate linker may the oxygen atom. The side chain may be linked to the aromatic structure via, for example, an oxygen atom or nitrogen.

In case where the aromatic structure is linked to the main chain of the block as a side chain, the aromatic structure may also be directly linked to the main chain or may be linked to the main chain via a linker. The linker may be an oxygen atom, a sulfur atom, —S(=O)$_2$—, a carbonyl group, an alkylene group, an alkenylene group, an alkynylene group, —C(=O)—X$_1$— or —X$_1$—C(=O)—. In the above, the X$_1$ may be a single bond, an oxygen atom, a sulfur atom, —S(=O)$_2$—, an alkylene group, an alkenylene group or alkynylene group. An appropriate linker boding the aromatic structure to the main chain may —C(=O)—O— or —O—C(=O)—, but is not limited thereto.

In another embodiment, the aromatic structure in the first block and/or the second block of the block copolymer may include 1 or more, 2 or more, 3 or more, 4 or more or 5 or more halogen atom(s). The number of the halogen atom(s) may be 30 or less, 25 or less, 20 or less, 15 or less or 10 or less. The halogen atom may be a fluorine or chlorine; and the fluorine may be used. The block comprising the aromatic structure including the halogen atom may effectively form the phase separation structure by an appropriate interaction with the other block.

As the aromatic structure including the halogen atom, an aromatic structure having 6 to 30, 6 to 25, 6 to 21, 6 to 18 or 6 to 13 carbon atoms may be illustrated, but is not limited thereto.

For realizing appropriate phase separations, in case where both of the first and second block include the aromatic structures, the first block may include an aromatic structure that does not include the halogen atom and the second block may include an aromatic structure that includes the halogen atom. Further, the aromatic structure of the first block may include the side chain that is linked directly or via the linker including the oxygen or nitrogen atom.

In case where the block copolymer includes the block having the side chain, the block may be a block represented by, for example, Formula 1.

[Formula 1]

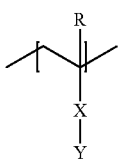

In Formula 1, the R may be hydrogen or an alkyl group having 1 to 4 carbon atom(s), the X may be a single bond, an oxygen atom, a sulfur atom, —S(=O)$_2$—, a carbonyl group, an alkylene group, an alkenylene group, an alkynylene group, —C(=O)—X$_1$— or —X$_1$—C(=O)—, wherein the X$_1$ may be an oxygen atom, a sulfur atom, —S(=O)$_2$—, an alkylene group, an alkenylene group or an alkynylene group, and the Y may be a monovalent substituent including a cyclic structure to which a chain having 8 or more chain-forming atoms is linked.

The term "single bond" as used herein may refer to a case where there is no atom in a corresponding site. For example, if the X in the Formula 1 is the single bond, a structure in which the Y is directly linked to the polymer chain may be realized.

The term "alkyl group" as used herein may refer to, unless defined otherwise, a linear, a branched or a cyclic alkyl group having 1 to 20, 1 to 16, 1 to 12, 1 to 8, or 1 to 4 carbon atoms, and the alkyl group may be optionally substituted with at least one substituent. In case where the side chain is the alkyl group, the alkyl group may include 8 or more, 9 or more, 10 or more, 11 or more or 12 or more carbon atoms, and the number of the carbon atoms in the alkyl group may be 30 or less, 25 or less, 20 or less or 16 or less.

The term "alkenyl or alkynyl group" as used herein may refer to, unless defined otherwise, a linear, a branched or a cyclic alkenyl or alkynyl group having 2 to 20, 2 to 16, 2 to 12, 2 to 8, or 2 to 4 carbon atoms and the alkenyl or alkynyl group may be optionally substituted with at least one substituent. In case where the side chain is the alkenyl or alkynyl group, the alkenyl or the alkynyl group may include 8 or more, 9 or more, 10 or more, 11 or more or 12 or more carbon atoms, and the number of the carbon atoms in the alkenyl or the alkynyl group may be 30 or less, 25 or less, 20 or less or 16 or less.

The term "alkylene group" as used herein may refer to, unless defined otherwise, an alkylene group having 1 to 20, 1 to 16, 1 to 12, 1 to 8 or 1 to 4 carbon atoms. The alkylene group may have a linear, branched, or cyclic structure, and may be optionally substituted with at least one substituent.

The term "alkenylene or alkynylene group" as used herein may refer to, unless defined otherwise, an alkenylene or alkynylene group having 2 to 20, 2 to 16, 2 to 12, 2 to 8 or 2 to 4 carbon atoms. The alkenylene or alkynylene group may have a linear, branched, or cyclic structure, and may be optionally substituted with at least one substituent.

The X of the Formula 1 may be, in another embodiment, —C(=O)O— or —OC(=O)—.

The Y in the formula 1 is the substituent including the chain, it may be a substituent including, for example, an aromatic structure having 6 to 18 or 6 to 12 carbon atoms. In the above, the chain may be an alkyl group having 8 or more, 9 or more, 10 or more, 11 or more or 12 or more carbon atoms. The alkyl group may include 30 or less, 25 or less, 20 or less or 16 or less carbon atom. The chain may be directly linked to the aromatic structure or be linked to the aromatic structure via the linker as described above.

The first block may be, in another embodiment, represented by the Formula 2 below.

[Formula 2]

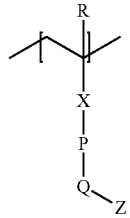

In Formula 2, the R may be the hydrogen atom or the alkyl group having 1 to 4 carbon atom(s), the X may be —C(=O)—O—, the P may be the arylene group having 6 to 12 carbon atoms, the Q may be the oxygen atom, the Z is the chain having 8 or more chain-forming atoms.

In another embodiment of the Formula 2, the P may be a phenylene. Also, the Z may be a linear alkyl group having 9 to 20, 9 to 18 or 9 to 16. In case where the P is the phenylene, the Q may be linked to the para position of the phenylene. The alkyl group, arylene group, phenylene group and the chain may be optionally substituted with at least one substituent.

In case where the block copolymer including the block comprising the aromatic structure comprising the halogen atom, the block may be a block represented by Formula 3 below.

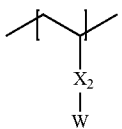

[Formula 3]

In Formula 3, the $X_2$ may be a single bond, an oxygen atom, a sulfur atom, —S(=O)$_2$—, an alkylene group, an alkenylene group, an alkynylene group, —C(=O)—$X_1$— or —$X_1$—C(=O)—, where the $X_1$ is a single bond, an oxygen atom, a sulfur atom, —S(=O)$_2$—, an alkylene group, an alkenylene group or an alkynylene group, and the W may be an aryl group including at least one halogen atom.

In another embodiment of the Formula 3, the $X_2$ may be the single bond or the alkylene group.

In the Formula 3, the aryl group of the W may be an aryl group having 6 to 12 carob atoms or a phenyl group. The aryl group or the phenyl group may include 1 or more, 2 or more, 3 or more, 4 or more or 5 or more halogen atom(s). The number of the halogen atom(s) may be 30 or less, 25 or less, 20 or less, 15 or less or 10 or less. As the halogen atom, fluorine atom may be used.

The block of the Formula 3 may be, in another embodiment, represented by Formula 4 below.

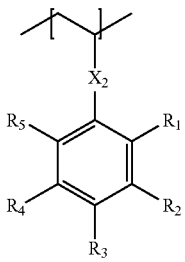

[Formula 4]

In Formula 4, the $X_2$ is the same as defined in the Formula 3, and the $R_1$ to $R_5$ may be each independently hydrogen, an alkyl group, a haloalkyl group or a halogen atom. The number of the halogen atom included in the $R_1$ to $R_5$ is 1 or more.

In Formula 4, the $R_1$ to $R_5$ may be each independently hydrogen, an alkyl group having 1 to 4 carbon atom(s) or a haloalkyl group having 1 to 4 carbon atom(s) or the halogen atom, and the halogen atom may be the fluorine or chlorine.

In Formula 4, the $R_1$ to $R_5$ may include 1 or more, 2 or more, 3 or more, 4 or more, 5 or more or 6 or more halogen atom(s). The upper limit of the number of the halogen atom(s) is not particularly limited, and the number of the halogen atom(s) in the $R_1$ to $R_5$ may be, for example, 12 or less, 8 or less, or 7 or less.

The block copolymer may include only the above described two kinds of blocks or may include one or both of the above described two kinds of blocks along with another block.

A method for preparing the block copolymer is not particularly limited. For example, the block copolymer may be prepared by a living radical polymerization (LRP). For example, there are methods such as the anionic polymerization, in which block copolymers are synthesized in the presence of inorganic acid salts such as salts of alkali metal or alkali earth metal by using organic rare earth metal complexes or organic alkali metal compounds as polymerization initiators; the anionic polymerization, in which block copolymers are synthesized in the presence of organic aluminum compounds by using organic alkali metal compounds as polymerization initiators; the atom-transfer radical polymerization (ATRP) using an atom transfer radical polymerizer as a polymerization controller; the activators regenerated by electron transfer (ATGET) ATRP performing polymerization in the presence of an organic or inorganic reducing agent generating electrons using an atom transfer radical polymerizer as a polymerization controller; the initiators for continuous activator regeneration (ICAR) ATRP; the reversible addition-ring opening chain transfer (RAFT) polymerization using an inorganic reducing agent reversible addition-ring opening chain transfer agent; and the a method using an organic tellurium compound as an initiator, and an appropriate method may be selected among the above methods.

In one embodiment, the block copolymer may be prepared by a method including polymerizing a material comprising monomers capable of forming the block in the presence of radical initiators and living radical polymerization reagents by the living radical polymerization. The method for preparing the block copolymer may further include, for example, precipitating the polymerized product formed from the above process in non solvent.

A kind of the radical initiators may be suitably selected in consideration of polymerization efficiency without particular limitation, and an azo compound such as azobisisobutyronitrile (AIBN) or 2,2'-azobis-(2,4-dimethylvaleronitrile), or a peroxide compound such as benzoyl peroxide (BPO) or di-t-butyl peroxide (DTBP) may be used.

The LRP may be performed in a solvent such as methylenechloride, 1,2-dichloroethane, chlorobenzene, dichlorobenzene, benzene, toluene, acetone, chloroform, tetrahydrofuran, dioxane, monoglyme, diglyme, dimethylformamide, dimethylsulfoxide or dimethylacetamide.

As the non-solvent, for example, an alcohol such as methanol, ethanol, normal propanol or isopropanol, a glycol such as ethyleneglycol, or an ether compound such as n-hexane, cyclohexane, n-heptane or petroleum ether may be used without limitation.

The block copolymer as described above may exhibit an excellent phase separation property and self assembling property and its vertical aligning property is also excellent. The present inventor has confirmed that, if the block copolymer further satisfies at least one parameter among ones as described below, the above properties can be further improved.

For example, the block copolymer may form a layer showing an in-plane phase diffraction pattern of the grazing incidence small angle X ray scattering (GISAXS) on a hydrophobic surface. The block copolymer may form a layer showing an in-plane phase diffraction pattern of the grazing incidence small angle X ray scattering (GISAXS) on a hydrophilic surface.

The term "showing the in-plane phase diffraction pattern of the grazing incidence small angle X ray scattering (GISAXS)" as used herein may refer to a case where a peak vertical to the X coordinate is observed in the GISAXS diffraction pattern when the GISAXS analysis is performed. Such a peak may be confirmed by the vertical aligning property of the block copolymer. Therefore, the block copolymer showing the in-plane phase diffraction pattern shows the vertical aligning property. Further, if the above peaks are observed with a regular interval, the phase separation efficiency may be further improved.

The term "vertical" as used herein is a term considering errors and, for example, it may include errors within ±10 degrees, ±8 degrees, ±6 degrees, ±4 degrees or ±2 degrees.

A block copolymer capable of forming a layer showing the in-plane phase diffraction patterns on both of the hydrophobic and the hydrophilic surfaces can show the vertical aligning property on various surface to which any treatment for inducing the vertical aligning is not performed. The term "hydrophobic surface" as used herein may refer to a surface of which a wetting angle of purified water is in a range from 5 degrees to 20 degrees. Examples of the hydrophobic surface may include a surface of silicone treated with the piranha solution, sulfuric acid, or an oxygen plasma, but is not limited thereto. The term "hydrophilic surface" as used herein may refer to a surface of which a wetting angle of purified water is in a range from 50 degrees to 70 degrees. Examples of the hydrophilic surface may include a surface of silicone treated with hydrogen fluoride, silicone treated with hexamethyldisilazane or polydimethylsiloxane treated with oxygen plasma, but is not limited thereto.

Unless defined otherwise, in this document, a property such as a wetting angle that can be changed according to temperature is measured at room temperature. The term "room temperature" as used herein may refer to a temperature in its natural state that is not heated and cooled and may refer to a temperature in a range from about 10° C. to 30° C., or of about 25° C. or about 23° C.

The layer that is formed on the hydrophobic or hydrophilic surface and shows the in-plane phase diffraction pattern on the GISAXS may be a layer to which a thermal annealing is performed. In one embodiment, the layer for measuring the GISAXS is, for example, prepared by coating a coating solution, which is prepared by diluting the block copolymer in a solvent (for example, fluorobenzene) to a concentration of about 0.7 weight %, on a corresponding hydrophobic or hydrophilic surface so as for the coated layer to have a thickness of about 25 nm and an area of about 2.25 cm$^2$ (a width: 1.5 cm, a length: 1.5 cm) and then performed the thermal annealing thereto. The thermal annealing may be performed by maintaining the layer for about 1 hour at a temperature of 160° C. The GISAXS may be measured by irradiating the above prepared layer with X ray so as for an incident angle thereof to be in a range from 0.12 to 0.23 degrees. Diffraction patterns scattered from the layer may be obtained by a conventional measuring device (for example, 2D marCCD). Techniques confirming the existence of the in-plane phase diffraction pattern from the above obtained diffraction pattern is known in the field.

The block copolymer showing the above peaks in the GISAXS can show excellent self assembling property and the property can be effectively controlled according to an object.

As described below, in case where at least one block of the block copolymer includes the side chain, the number (n) of the chain-forming atoms and the scattering vector (q) obtained from the XRD analysis may satisfy the equation 1 below.

$$3 \text{ nm}^{-1} \sim 5 \text{ nm}^{-1} = nq/(2 \times \pi) \quad \text{[Equation 1]}$$

In the Equation 1, the "n" is the number of the chain-forming atoms, and the "q" is the smallest scattering vector among scattering vectors at which peaks are observed in the XRD analysis or a scattering vector at which a peak having the largest area is observed. Further, the $\pi$ in the equation 1 is the ratio of the circumference of a circle to its diameter.

The scattering vectors and the like in the above equation 1 are values obtained by the same method as described in the XRD analysis.

The scattering value substituted with the value of the equation 1 may be a scattering value within a range from 0.5 nm$^{-1}$ to 10 nm$^{-1}$. In another embodiment, the scattering value substituted with the value of the equation 1 may be a scattering value within a range from 0.5 nm$^{-1}$ to 10 nm$^{-1}$. In another embodiment, the scattering value substituted with the value of the equation 1 may be 0.7 nm$^{-1}$ or more, 0.9 nm$^{-1}$ or more, 1.1 nm$^{-1}$ or more, 1.3 nm$^{-1}$ or more or 1.5 nm$^{-1}$ or more. In another embodiment, the scattering value substituted with the value of the equation 1 may be 9 nm$^{-1}$ or less, 8 nm$^{-1}$ or less, 7 nm$^{-1}$ or less, 6 nm$^{-1}$ or less, 5 nm$^{-1}$ or less, 4 nm$^{-1}$ or less, 3.5 nm$^{-1}$ or less or 3 nm$^{-1}$ or less.

The equation 1 may represent a relation between the number of the chain-forming atoms and an interval (D) between blocks including the chains under a state where the block copolymer is self assembled and forms the phase separated structure. If the number of the chain-forming atoms of the block copolymer including the chains satisfies the equation 1, the crystallizability exhibited by the chain is improved, and therefore the phase separation property and the vertical aligning property may be largely improved. In another embodiment, the $nq/(2 \times \pi)$ in the equation 1 may be 4.5 nm$^{-1}$ or less. In the above, the interval (D, unit: nm) between blocks including the chains can be calculated by a numerical formula, $D = 2 \times \pi / q$. In the above, the "D" is the interval (D, unit: nm) between the blocks and the $\pi$ and the q are the same as defined in the equation 1.

In one embodiment of the present application, an absolute value of a difference between surface energies of the first and the second blocks may be 10 mN/m or less, 9 mN/m or less, 8 mN/m or less, 7.5 mN/m or less or 7 mN/m or less. The absolute value of the difference between surface energies may be 1.5 mN/m or more, 2 mN/m or more or 2.5 mN/m or more. The structure in which the first and the second blocks, the absolute value of the difference between the surface energies of which is within the above range, are linked via the covalent bond may realize an effective microphase separation by a phase separation due to appropriate un-compatibilities. In the above, the first block may be the block having the chain as described above.

The surface energy may be measured by using a drop shape analyzer (DSA100 product manufactured in KRUSS, Co.). Specifically, the surface energy may be measured with respect to a layer prepared by coating a coating solution prepared by diluting a sample (a block copolymer or a homopolymer) to be measured in fluorobenzene to a solid content of about 2 weight % on a substrate so as for the coated layer to have a thickness of 50 nm and a coated area of 4 cm$^2$ (a width: 2 cm, a length: 2 cm); drying the coated layer for about an hour at the room temperature; and then performing a thermal annealing for about an hour at 160° C. On the layer after the thermal annealing is performed, deionized water of which the surface tension is known is dropped and then the contact angle is measured. The above process for obtaining the contact angle of the deionized water is repeated 5 times, and the average value of the 5 obtained contact angles are calculated. Identically, on the layer after the thermal annealing is performed, diiodomethane of which the surface tension is known is dropped and then the contact angle is measured. The above process for obtaining the contact angle of the diiodomethane is repeated 5 times, and the average value of the 5 obtained contact angles are calculated. After that, the surface energy may be obtained by substituting a value (Strom value) regarding the surface tension of the solvent through the Owens-Wendt-Rabel-Kaelble method using the obtained average values of the contact angles of the deionized water and the diiodomethane. The surface energy of each block in the block copolymer may be obtained by using the above described method with respect to a homopolymer prepared by monomers forming the corresponding block.

In case where the block copolymer comprises the above described chain, the block comprising the chain may have a larger surface energy than the other block. For example, if the first block comprises the chain, the first block may have a larger surface energy than the second block. In this case, the surface energy of the first block may be in a range from about 20 mN/m to about 40 mN/m. In another embodiment, the surface energy of the first block may be about 22 mN/m or more, about 24 mN/m or more, about 26 mN/m or more or about 28 mN/m or more. The surface energy of the first block may be about 38 mN/m or less, about 36 mN/m or less, about 34 mN/m or less or about 32 mN/m or less. Such a block copolymer including the above first block and showing the above difference between surface energies of blocks may show an excellent self assembling property.

In the block copolymer, an absolute value of a difference between densities of the first and the second blocks may be 0.25 g/cm$^3$ or more, 0.3 g/cm$^3$ or more, 0.35 g/cm$^3$ or more, 0.4 g/cm$^3$ or more or 0.45 g/cm$^3$ or more. The absolute value of the difference between the densities may be 0.9 g/cm$^3$ or less, 0.8 g/cm$^3$ or less, 0.7 g/cm$^3$ or less, 0.65 g/cm$^3$ or less or 0.6 g/cm$^3$ or less. The structure in which the first and the second blocks, the absolute value of the difference between the densities of which is within the above range, are linked via the covalent bond may realize an effective microphase separation by a phase separation due to appropriate un-compatibilities.

The density of each block in the block copolymer may be obtained through a known buoyancy method. For example, it may be obtained by analyzing a mass of a block copolymer in solvent such as ethanol, of which a mass and a density in the air are known.

In case where the block copolymer comprises the above described side chain, the block comprising the chain may have a lower density than the other block. For example, if the first block comprises the chain, the first block may have a lower density than the second block. In this case, the density of the first block may be in a range from about 0.9 g/cm$^3$ to about 1.5 g/cm$^3$. In another embodiment, the density of the first block may be about 0.95 g/cm$^3$ or more. The density of the first block may be about 1.4 g/cm$^3$ or less, about 1.3 g/cm$^3$ or less, about 1.2 g/cm$^3$ or less, about 1.1 g/cm$^3$ or less or about 1.05 g/cm$^3$ or less. Such a block copolymer including the above first block and showing the above difference between the densities of blocks may show an excellent self assembling property. The surface energy and the density are measured at the room temperature.

The block copolymer may include a block, of which a volume fraction is from 0.4 to 0.8, and a block, of which a volume fraction is from 0.2 to 0.6. In case where the block copolymer comprises the chain, the block having the chain may have the volume fraction from 0.4 to 0.8. For example, the first block comprises the chain, the first block may have the volume fraction from 0.4 to 0.8 and the second block may have the volume fraction from 0.2 to 0.6. The sum of the volume fractions of the first and the second blocks may be 1. The block copolymer including each block in the above volume fractions may show an excellent self assembling property. The volume fraction of each block of the block copolymer may be obtained by using the density of each block and a molecular weight obtained by the Gel Permeation Chromatograph (GPC).

The block copolymer may have, for example, a number average molecular weight (Mn) in a range from approximately 3,000 to 300,000. The term "number average molecular weight" as used herein may refer to a converted value with respect to the standard polystyrene measured by the GPC (Gel Permeation Chromatography). Unless defined otherwise, the term "molecular weight" as used herein may refer to the number average molecular weight. The molecular weight (Mn), in another embodiment, may be, for example, 3000 or more, 5000 or more, 7000 or more, 9000 or more, 11000 or more, 13000 or more or 15000 or more. The molecular weight (Mn), in another embodiment, may be, for example, 250000 or less, 200000 or less, 180000 or less, 160000 or less, 140000 or less, 120000 or less, 100000 or less, 90000 or less, 80000 or less, 70000 or less, 60000 or less, 50000 or less, 40000 or less, 30000 or less, or 25000 or less. The block copolymer may have the polydispersity (Mw/Mn) in a range from 1.01 to 1.60. In another embodiment, the polydispersity may be about 1.1 or more, about 1.2 or more, about 1.3 or more, or about 1.4 or more.

In the above range, the block copolymer may exhibit an appropriate self assembling property. The number average molecular weight and the like of the block copolymer may be controlled considering the objected self assembled structure.

If the block copolymer at least includes the first and second blocks, a ratio of the first block, for example, the block including the chain in the block copolymer may be in a range of 10 mole % to 90 mole %.

The present application relates to a polymer layer including the block copolymer. The polymer layer may be used in various applications. For example, it can be used in a biosensor, a recording media such as a flash memory, a magnetic storage media or the pattern forming method or an electric device or an electronic device, and the like.

In one embodiment, the block copolymer in the polymer layer may be forming a periodic structure including a sphere, a cylinder, a gyroid, or a lamella by the self assembly. For example, in one segment of the first block or the second block or other block linked to the above block via a covalent bond in the block copolymer, other segment may be forming the regular structure such as lamella form, cylinder form and the like. And the above structure may be aligned vertically.

The polymer layer may show the above in-plane phase diffraction pattern, i.e., the peak vertical to the X coordinate in the GISAXS diffraction pattern of the GISAXS analysis. In further embodiment, two or more peaks may be observed in the X coordinate of the GISAXS diffraction pattern. In case where two or more peaks are observed, the scattering vectors (the q values) may be confirmed with having constant ratios.

The present application relates also to a method for forming a polymer layer by using the block copolymer. The method may include forming a polymer layer including the block copolymer on a substrate in a self-assembled state. For example, the method may include forming a layer of the block copolymer or a coating solution in which the block copolymer is diluted in suitable solvent on the substrate by a coating and the like, and if necessary, then aging or heat-treating the layer.

The aging or the heat treatment may be performed based on, for example, a phase transition temperature or glass transition temperature of the block copolymer, and for example, may be performed at a temperature higher than the glass transition temperature or phase transition temperature. A time for the heat treatment is not particularly limited, and the heat treatment may be performed for approximately 1 minute to 72 hours, but may be changed if necessary. In addition, the temperature of the heat treatment of the polymer layer may be, for example, 100° C. to 250° C., but may be changed in consideration of the block copolymer used herein.

The formed layer may be aged in a non-polar solvent and/or a polar solvent at the room temperature for approximately 1 minute to 72 hours.

The present application relates also to a pattern-forming method. The method may include selectively removing the first or second block of the block copolymer from a laminate comprising a substrate and a polymer layer that is formed on a surface of the substrate and that includes a self-assembled block copolymer. The method may be a method for forming a pattern on the above substrate. For example, the method may include forming the polymer layer on the substrate, selectively removing one block or two or more blocks of the block copolymer that is in the polymer layer; and then etching the substrate. By the above method, for example, nano-scaled micropattern may be formed. Further, according to shapes of the block copolymer in the polymer layer, various shapes of pattern such as nano-rod or nano-hole can be formed by the above method. If necessary, in order to form a pattern, the block copolymer may be mixed with another copolymer or homopolymer. A kind of the substrate applied to this method may be selected without particular limitation, and, for example, silicon oxide and the like may be applied.

For example, according to the method, a nano-scale pattern of silicon oxide having a high aspect ratio may be formed. For example, various types of patterns such as a nanorod or nanohole pattern may be formed by forming the polymer layer on the silicon oxide, selectively removing any one block of the block copolymer in a state where the block copolymer in the polymer layer is formed in a predetermined structure, and etching the silicon oxide in various methods, for example, reactive ion etching. In addition, according to the above method, a nano pattern having a high aspect ratio can be formed.

For example, the pattern may be formed to a scale of several tens of nanometers, and such a pattern may be applied in various uses including a next-generation information electronic magnetic recording medium.

For example, a pattern in which nano structures, for example, nanowires, having a width of approximately 3 to 40 nm are disposed at an interval of approximately 6 to 80 nm may be formed by the above-described method. In another embodiment, a structure in which nanoholes having a width, for example, a diameter of approximately 3 to 40 nm are disposed at an interval of approximately 6 to 80 nm can be implemented.

In addition, in this structure, nanowires or nanoholes may be formed to have a high aspect ratio.

In this method, a method of selectively removing any one block of the block copolymer is not particularly limited, and for example, a method of removing a relatively soft block by irradiating a suitable electromagnetic wave, for example, ultra violet rays to a polymer layer may be used. In this case, conditions for ultra violet radiation may be determined according to a type of the block of the block copolymer, and ultra violet rays having a wavelength of approximately 254 nm may be irradiated for 1 to 60 minutes.

In addition, followed by the ultra violet radiation, the polymer layer may be treated with an acid to further remove a segment degraded by the ultra violet rays.

In addition, the etching of the substrate using the polymer layer from which a block is selectively removed may be performed by reactive ion etching using $CF_4$/Ar ions, and followed by the above process, and removing the polymer layer from the substrate by oxygen plasma treatment may be further performed.

BRIEF DESCRIPTION OF FIGURES

FIGS. 1 to 5 are the SEM images of Examples 1 to 5, respectively. FIG. 6 is the SEM image of Comparative Example 3.

FIG. 7 shows the result of the GISAXS (Grazing Incident Small Angle X ray Scattering) analysis of the block copolymer of Example 1 performed with respect to the surface of which a contact angle at the room temperature with respect to the purified water was about 5 degrees. FIG. 8 shows the result of the GISAXS (Grazing Incident Small Angle X ray Scattering) analysis of the block copolymer of Example 1 performed with respect to the surface of which a contact angle at the room temperature with respect to the purified water was about 60 degrees.

FIGS. 9 to 11 are the SEM images regarding the polymer layers on the surface having the contact angles of 5 degrees, 45 degrees and 60 degrees, respectively.

FIGS. 12 to 14 are the GISAXS results of the samples 1 to 3, respectively.

EFFECTS

Figure 1:
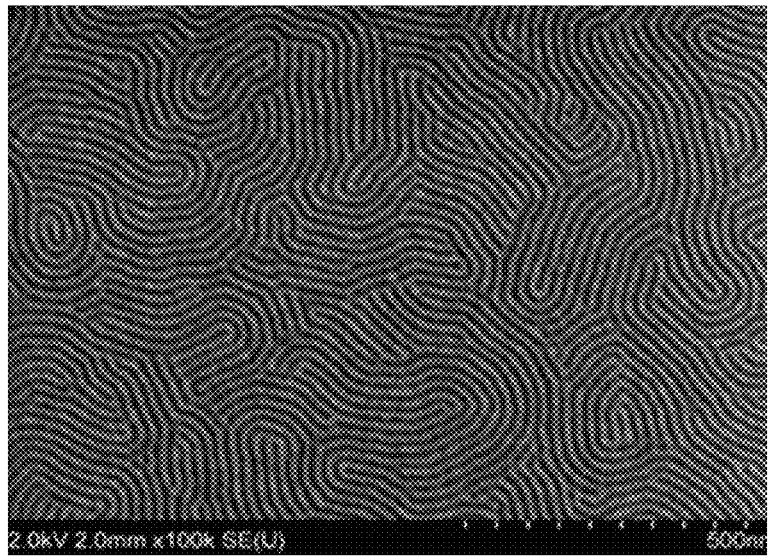
FIGS. 1 to 6 show SEM images of polymer layers.
Figure 2:
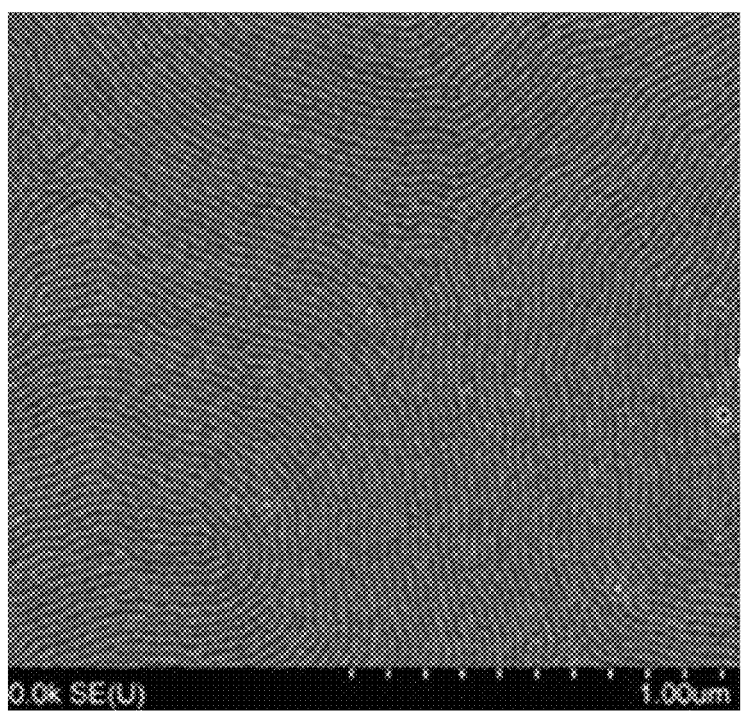
Figure 3:
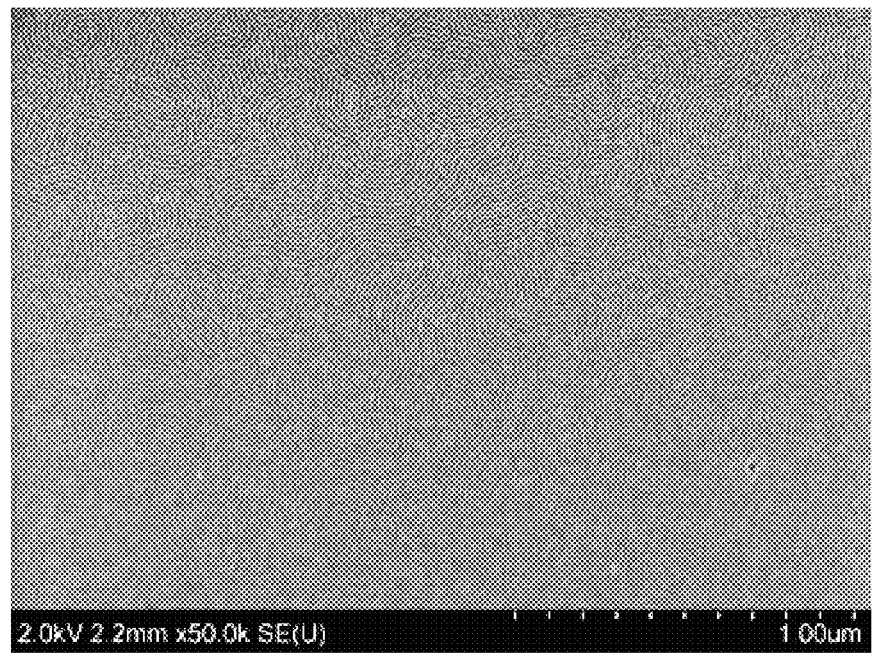
Figure 4:
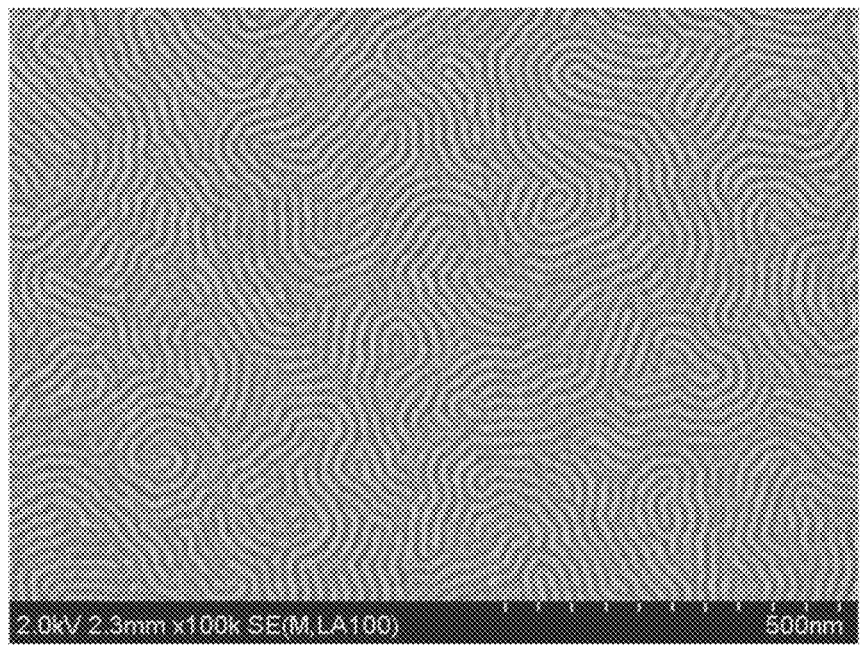
Figure 5:
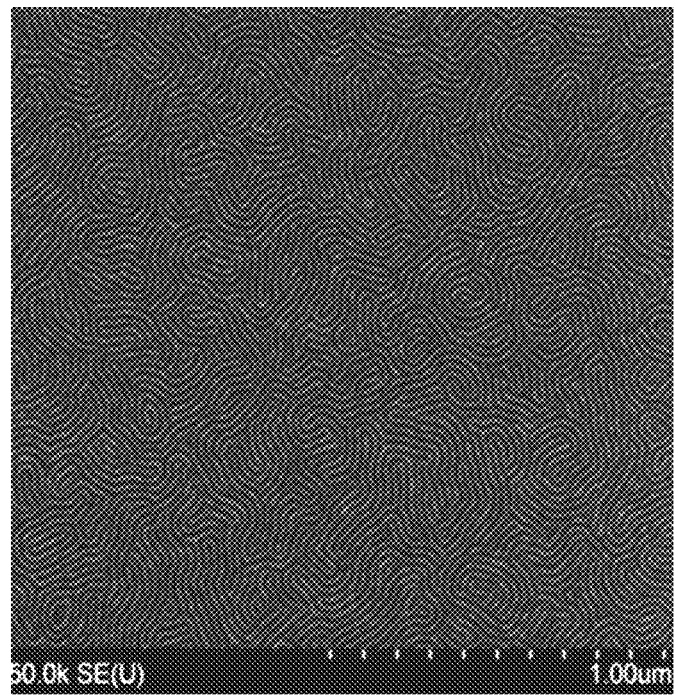

The present application may provide the block copolymers that have excellent self assembling and phase separation properties and therefore that can be effectively used in various applications. The present application may also provide applications of the block copolymers.

Illustrative Embodiments

Hereinafter, the present application will be described in detail with reference to Examples and Comparative Examples, but the scope of the present application is not limited to the following examples.

1. NMR Analysis

The NMR analysis was performed at the room temperature by using a NMR spectrometer including a Varian Unity Inova (500 MHz) spectrometer having a triple resonance 5 mm probe. A sample to be analyzed was used after diluting it in solvent ($CDCl_3$) for the NMR analysis to a concentration of approximately 10 mg/ml and a chemical shift (δ) was expressed in ppm.

<Abbreviation> br=wide signal, s=singlet, d=doublet, dd=double doublet, t=triplet, dt=double triplet, q=quadruplet, p=quintuplet, m=multiplet 2. GPC (Gel Permeation Chromatograph)

The number average molecular weight and the polydispersity were measured by the GPC (Gel Permeation Chromatograph). In a 5 mL vial, a block copolymer or a macroinitiator to be measured of Example or Comparative Example and then diluted to a concentration of about 1 mg/mL. Then, the standard sample for a calibration and a sample to be analyzed were filtered by a syringe filter (pore size: 0.45 μm) and then analyzed. ChemStation from the Agilent technologies, Co. was used as an analysis program. The number average molecular weight (Mn) and the weight average molecular weight (Mw) were obtained by comparing an elution time of the sample with a calibration curve and then the polydispersity (PDI) was obtained from their ratio (Mw/Mn). The measuring condition of the GPC was as below.

<GPC Measuring Condition>
Device: a 1200 series from Agilent technologies, Co.
Column: two of PLgel mixed B from Polymer laboratories, Co. were used
Solvent: THF
Temperature of the column: 35° C.
Concentration of Sample: 1 mg/mL, 200 L injection
Standard Sample: Polystyrene (Mp: 3900000, 723000, 316500, 52200, 31400, 7200, 3940, 485)

3. GISAXS (Grazing Incidence Small Angle X Ray Scattering)

The GISAXS analysis was performed in a 3 C beam line of the Pohang Light Source. A coating solution was prepared by dissolving a block copolymer to be evaluated in fluorobenzene so as for a solid content to be 0.7 weight %, the coating solution was spin coated on a substrate so as to having a thickness of about 5 nm. The coating area was controlled to be about 2.25 cm$^2$ (coated area: width=1.5 cm, length=1.5 cm). The coated layer was dried for about 1 hour at the room temperature and then subjected to the thermal annealing at about 160° C. for about 1 hour so as for the phase separation structure to be realized. Therefore, the layer in which the phase separation structure was realized was formed. The formed layer was irradiated with X ray so as for an incident angle to be from about 0.12 degrees to 0.23 degrees, which corresponded to an angle between a critical angle of the layer and a critical angle of the substrate, and then the X ray diffraction pattern scattered from the layer was obtained by using a 2D marCCD. At this time, a distance from the layer to the detector was selected so as for the self assembled pattern in the layer to be effectively observed within a range from about 2 m to 3 m. As the substrate, a substrate (a silicone substrate that was treated with piranha solution and that has a wetting angle of about 5 degrees with respect to purified water at the room temperature) having the hydrophilic surface or a substrate (a silicone substrate that was treated with HMDS (hexamethyldisilazane) and that has a wetting angle of about 60 degrees with respect to purified water at the room temperature) having the hydrophobic surface was used.

4. XRD Analysis

The XRD pattern was evaluated by measuring the scattering intensity according to the scattering vector (q) by passing X ray through a sample in a 4 C beam line of the Pohang Light Source. As the sample, powder obtained from the block copolymer to which any specific pre-treatment was not performed by purifying it so as to remove impurities therefrom was used after putting it in a cell for measurement of the XRD. During the XRD pattern analysis, as the X ray, X ray, a vertical size of which is 0.023 mm and a horizontal size of which is 0.3 mm was used and, as the detector, the measuring device (for example, 2D marCCD) was used. A 2D diffraction pattern scattered from the sample was obtained as an image. Information such as the scattering vectors and the FWHMs was obtained by analyzing the obtained diffraction pattern by the numerical analysis using the least square technique. The analysis was performed by the origin program. A position at which the XRD diffraction pattern had the lowest intensity became the baseline and the lowest intensity was converted to zero, and then the Gaussian fitting was performed with respect to the profile of peaks in the XRD pattern, and then the scattering vector (q) and the FWHM were obtained from the result of the Gaussian fitting. The R square of the Gaussian fitting was set to be 0.96 or more.

5. Surface Energies Measurement

The surface energy was measured by using the drop shape analyzer (DSA 100 product from KRUSS, Co.). The surface energy was evaluated with respect to the polymer layer formed by spin-coating a coating solution, which was prepared by dissolving the material to be evaluated in fluorobenzene so as for a solid content to be 2 weight %, on a silicone wafer so as for the coated layer to have a thickness of 50 nm (coated area: width=2 cm, length=2 cm) and drying it for about 1 hour at the room temperature and then subjecting it to the thermal annealing at about 160° C. for about 1 hour. A process, in which deionized water of which the surface tension is known was dropped on the layer after the thermal annealing and then its contact angle was obtained, was repeated 5 times, and an average value of the obtained 5 contact angles was calculated. Identically, a process, in which diiodomethane of which the surface tension is known was dropped on the layer after the thermal annealing and then its contact angle was obtained, was repeated 5 times, and an average value of the obtained 5 contact angles was calculated. The surface energy was obtained by the Owens-Wendt-Rabel-Kaelble method by using the obtained average values of the contact angles of the deionized water and the diiodomethane and substituting a value (the Strom value) regarding the surface tension of solvent. The surface energy of each block of the block copolymer was obtained as above with respect to a homopolymer prepared only by monomers forming the block.

6. Volume Fraction Measurement

The volume fraction of each block of the block copolymer was calculated based on a molecular weight measured by a GPC (Gel Permeation Chromatograph) and the density at the room temperature. In the above, the density was measured by the buoyancy method, specifically, was calculated by a mass of a sample to be measured in solvent (ethanol), of which a mass and a density in the air are known.

PREPARATION EXAMPLE 1

Synthesis of a Monomer (A)

A compound (DPM-C12) of the Formula A below was synthesized by the below method. To a 250 mL flask, hydroquinone (10.0 g, 94.2 mmole) and 1-bromododecane (23.5 g, 94.2 mmole) were added and dissolved in 100 mL acetonitrile, an excessive amount of potassium carbonate was added thereto and then the mixture was reacted at 75° C. for approximately 48 hours under nitrogen. After the reaction, remaining potassium carbonate and acetonitrile used for the reaction were removed. The work up was performed by adding a mixed solvent of dichloromethane (DCM) and water, and separated organic layers were collected and dehydrated through MgSO$_4$. Subsequently, a white solid intermediate was obtained with a yield of approximately 37% using DCM through column chromatography.

<NMR Analysis Result of the Intermediate>
$^1$H-NMR (CDCl$_3$): δ6.77(dd, 4H); δ4.45(s, 1H); δ3.8(t, 2H); δ1.75(p, 2H); δ1.43(p, 2H); δ1.33-1.26(m, 16H); δ0.88 (t, 3H)

The synthesized intermediate (9.8 g, 35.2 mmole), methacrylic acid (6.0 g, 69.7 mmole), dicyclohexylcarbodiimide (DCC; 10.8 g, 52.3 mmole) and p-dimethylaminopyridine (DMPA; 1.7 g, 13.9 mmol) were put into a flask, 120 ml of methylenechloride was added, and a reaction was performed at the room temperature for 24 hours under nitrogen. After the reaction was completed, a urea salt produced in the reaction was removed through a filter, and remaining methylenechloride was also removed. Impurities were removed using hexane and DCM (dichloromethane) as mobile phases though column chromatography, and the obtained product was recrystallized in a mixed solvent of methanol and water (mixed in 1:1 weight ratio), thereby obtaining a white solid product (DPM-C12)(7.7 g, 22.2 mmol) with a yield of 63%.

<NMR Analysis Result>

$^1$H-NMR (CDCl$_3$): δ7.02(dd, 2H); δ6.89(dd, 2H); δ6.32 (dt, 1H); δ5.73(dt, 1H); δ3.94(t, 2H); δ2.05(dd, 3H); δ1.76 (p, 2H); δ1.4(p, 2H); 1.34-1.27(m, 16H); δ0.88(t, 3H)

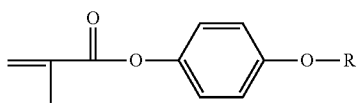

[Formula A]

In the above, the R is a linear alkyl having 12 carbon atoms.

PREPARATION EXAMPLE 2

Synthesis of a Monomer (G)

A compound of the Formula G below was synthesized according to the method of Preparation Example 1, except that 1-bromobutane was used instead of the 1-bromododecane. The NMR analysis result with respect to the above compound is as below.

<NMR analysis result with respect to DPM-C4>

$^1$H-NMR (CDCl$_3$): δ7.02(dd, 2H); δ6.89(dd, 2H); δ6.33 (dt, 1H); δ5.73dt, 1H); δ3.95(t, 2H); δ2.06(dd, 3H); δ1.76(p, 2H); δ1.49(p, 2H); δ0.98(t, 3H)

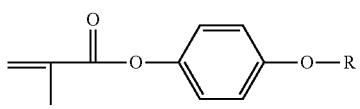

[Formula G]

In the above, the R is a linear alkyl having 4 carbon atoms.

PREPARATIVE EXAMPLE 3

Synthesis of a Monomer (B)

A compound of the Formula B below was synthesized according to the method of Preparation Example 1, except that 1-bromooctane was used instead of the 1-bromododecane. The NMR analysis result with respect to the above compound is as below.

<NMR Analysis Result with Respect to DPM-C8>

$^1$H-NMR (CDCl$_3$): δ7.02(dd, 2H); δ6.89(dd, 2H); δ6.32 (dt, 1H); δ5.73(dt, 1H); δ3.94(t, 2H); δ2.05(dd, 3H); δ1.76 (p, 2H); δ1.45(p, 2H); 1.33-1.29(m, 8H); δ0.89(t, 3H)

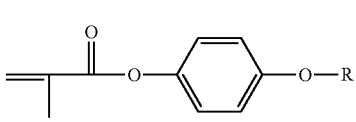

[Formula B]

In the above, the R is a linear alkyl having 8 carbon atoms.

PREPARATION EXAMPLE 4

A compound (DPM-C10) of the Formula C below was synthesized according to the method of Preparation Example 1, except that 1-bromodecane was used instead of the 1-bromododecane. The NMR analysis result with respect to the above compound is as below.

<NMR Analysis Result with Respect to DPM-C10>

$^1$H-NMR (CDCl$_3$): δ7.02(dd, 2H); δ6.89(dd, 2H); δ6.33 (dt, 1H); δ5.72(dt, 1H); δ3.9(t, 2H); δ2.06(dd, 3H); δ1.77(p, 2H); δ1.45(p, 2H); 1.34-1.28(m, 12H); δ0.89(t, 3H)

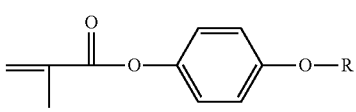

[Formula C]

In the above, the R is a linear alkyl having 10 carbon atoms.

PREPARATION EXAMPLE 5

A compound of the Formula D below was synthesized according to the method of Preparation Example 1, except that 1-bromotetradecane was used instead of the 1-bromododecane. The NMR analysis result with respect to the above compound is as below.

<NMR Analysis Result with Respect to DPM-C14>

$^1$H-NMR (CDCl$_3$): δ7.02(dd, 2H); δ6.89(dd, 2H); δ6.33 (dt, 1H); δ5.73(dt, 1H); δ3.94(t, 2H); δ2.05(dd, 3H); δ1.77 (p, 2H); δ1.45(p, 2H); 1.36-1.27(m, 20H); δ0.88(t, 3H.)

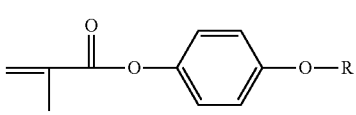

[Formula D]

In the above, the R is a linear alkyl having 14 carbon atoms.

PREPARATION EXAMPLE 6

A compound of the Formula E below was synthesized according to the method of Preparation Example 1, except that 1-bromohexadecane was used instead of the 1-bromododecane. The NMR analysis result with respect to the above compound is as below.

<NMR Analysis Result with Respect to DPM-C16>

$^1$H-NMR (CDCl$_3$): δ7.01(dd, 2H); δ6.88(dd, 2H); δ6.32 (dt, 1H); δ5.73(dt, 1H); δ3.94(t, 2H); δ2.05(dd, 3H); δ1.77 (p, 2H); δ1.45(p, 2H); 1.36-1.26(m, 24H); δ0.89(t, 3H)

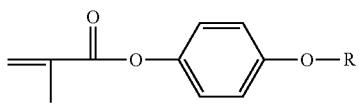

[Formula E]

In the above, the R is a linear alkyl having 16 carbon atoms.

EXAMPLE 1

2.0 g of the compound (DPM-C12) of Preparation Example 1, 64 mg of RAFT (Reversible Addition-Fragmentation chain transfer) reagent (cyanisopropyl dithiobenzoate), 23 mg of AIBN (azobisisobutyronitrile) and 5.34 mL of benzene were added to a 10 mL flask and then were stirred at the room temperature for 30 minutes and then the RAFT (reversible addition fragmentation chain transfer) polymerization was performed at 70° C. for 4 hours. After the polymerization, the reacted solution was precipitated in 250 mL of methanol that was an extraction solvent, was vacuum filtered and dried so as to obtain pink macroinitiator. The yield of the macroinitiator was about 86%, and its number average molecular weight (Mn) and polydispersity (Mw/Mn) were 9,000 and 1.16, respectively.

0.3 g of the macroinitiator, 2.7174 g of pentafluorostyrene and 1.306 mL of benzene were added to a 10 mL Schlenk flask and then were stirred at the room temperature for 30 minutes and then the RAFT (reversible addition fragmentation chain transfer) polymerization was performed at 115° C. for 4 hours. After the polymerization, the reacted solution was precipitated in 250 mL of methanol that was an extraction solvent, was vacuum filtered and dried so as to obtain light pink block copolymer. The yield of the block copolymer was about 18%, and its number average molecular weight (Mn) and polydispersity (Mw/Mn) were 16,300 and 1.13, respectively. The block copolymer includes the first block derived from the monomer (A) of Preparation Example 1 and the second block derived from the pentafluorostyrene.

EXAMPLE 2

A block copolymer was prepared by the same method as in Example 1 except that a macroinitiator prepared by using the monomer (B) of Preparation Example 3 instead of the monomer (A) of Preparation Example 1 and pentafluorostyrene were used. The block copolymer includes the first block derived from the monomer (B) of Preparation Example 3 and the second block derived from the pentafluorostyrene.

EXAMPLE 3

A block copolymer was prepared by the same method as in Example 1 except that a macroinitiator prepared by using the monomer (C) of Preparation Example 4 instead of the monomer (A) of Preparation Example 1 and pentafluorostyrene were used. The block copolymer includes the first block derived from the monomer (C) of Preparation Example 4 and the second block derived from the pentafluorostyrene.

EXAMPLE 4

A block copolymer was prepared by the same method as in Example 1 except that a macroinitiator prepared by using the monomer (D) of Preparation Example 5 instead of the monomer (A) of Preparation Example 1 and pentafluorostyrene were used. The block copolymer includes the first block derived from the monomer (D) of Preparation Example 5 and the second block derived from the pentafluorostyrene.

EXAMPLE 5

A block copolymer was prepared by the same method as in Example 1 except that a macroinitiator prepared by using the monomer (E) of Preparation Example 6 instead of the monomer (A) of Preparation Example 1 and pentafluorostyrene were used. The block copolymer includes the first block derived from the monomer (E) of Preparation Example 6 and the second block derived from the pentafluorostyrene.

COMPARATIVE EXAMPLE 1

A block copolymer was prepared by the same method as in Example 1 except that a macroinitiator prepared by using the monomer (G) of Preparation Example 2 instead of the monomer (A) of Preparation Example 1 and pentafluorostyrene were used. The block copolymer includes the first block derived from the monomer (G) of Preparation Example 2 and the second block derived from the pentafluorostyrene.

COMPARATIVE EXAMPLE 2

A block copolymer was prepared by the same method as in Example 1 except that a macroinitiator prepared by using 4-methoxyphenyl methacrylate instead of the monomer (A) of Preparation Example 1 and pentafluorostyrene were used. The block copolymer includes the first block derived from the 4-methoxyphenyl methacrylate and the second block derived from the pentafluorostyrene.

COMPARATIVE EXAMPLE 3

A block copolymer was prepared by the same method as in Example 1 except that a macroinitiator prepared by using dodecyl methacrylate instead of the monomer (A) of Preparation Example 1 and pentafluorostyrene were used. The block copolymer includes the first block derived from the dodecyl methacrylate and the second block derived from the pentafluorostyrene.

The GPC results regarding the macroinitiator and the block copolymer of the Examples are stated in Table 1.

TABLE 1

| | | Examples | | | | | Com. Examples | | |
| --- | --- | --- | --- | --- | --- | --- | --- | --- | --- |
| | | 1 | 2 | 3 | 4 | 5 | 1 | 2 | 3 |
| MI | Mn | 9000 | 9300 | 8500 | 8700 | 9400 | 9000 | 7800 | 8000 |
| | PDI | 1.16 | 1.15 | 1.17 | 1.16 | 1.13 | 1.16 | 1.17 | 1.19 |

TABLE 1-continued

|  |  | Examples | | | | | Com. Examples | | |
| --- | --- | --- | --- | --- | --- | --- | --- | --- | --- |
|  |  | 1 | 2 | 3 | 4 | 5 | 1 | 2 | 3 |
| BCP | Mn | 16300 | 19900 | 17100 | 17400 | 18900 | 18800 | 18700 | 16700 |
|  | PDI | 1.13 | 1.20 | 1.19 | 1.17 | 1.17 | 1.22 | 1.25 | 1.18 |

MI: the macroinitiator
BCP: the block copolymer
Mn: the number average molecular weight
PDI: the polydispersity

TEST EXAMPLE 1

XRD Analysis

The result of the XRD analysis performed regarding the block copolymer according to the above method is stated in Table 2 below (In case of the Comparative Example 3, no peak was observed in a range of the scattering vectors from 0.5 nm$^{-1}$ to 10 nm$^{-1}$).

TABLE 2

|  | Exs. | | | | | Com. Exs. | | |
| --- | --- | --- | --- | --- | --- | --- | --- | --- |
|  | 1 | 2 | 3 | 4 | 5 | 1 | 2 | 3 |
| Scattering vector (the q value) (unit: nm$^{-1}$) | 1.96 | 2.41 | 2.15 | 1.83 | 1.72 | 4.42 | 3.18 | — |
| FWHM (unit: nm$^{-1}$) | 0.57 | 0.72 | 0.63 | 0.45 | 0.53 | 0.97 | 1.06 | — |

TEST EXAMPLE 1

Figure 6:
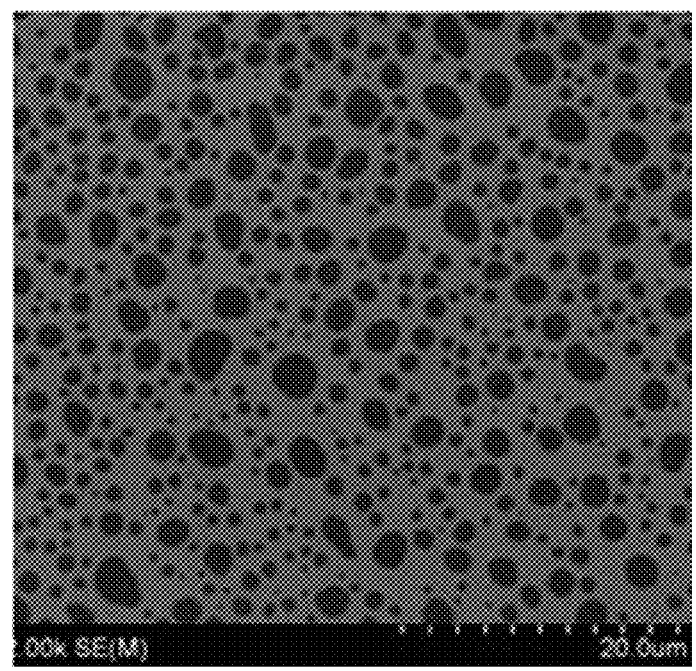

The self assembled polymer layer was obtained by spin coating a coating solution prepared by dissolving the block copolymer of Examples or Comparative Examples in fluorobenzene on a silicone wafer so as for a coated thickness to be 5 nm (a coated area: a width×a length=1.5 cm×1.5 cm), and drying it for 1 hour at the room temperature and then subjecting it to a thermal annealing for 1 hour at about 160° C. Then, a SEM (scanning electron microscope) image of the formed polymer layer was obtained. FIGS. 1 to 5 are results of Examples 1 to 5, respectively. As confirmed from Figures, in case of the block copolymers of Examples, self assembled polymer layer having line patterns are effectively formed. However, an appropriate phase separation was not realized in Comparative Example. For example, FIG. 6 is the SEM result of Comparative Example 3, and it is confirmed that effective phase separation was not realized.

TEST EXAMPLE 2

GISAXS Diffraction Pattern Confirmation

Figure 7:
FIGS. 7 and 8 show GISAXS diffraction pattern.
Figure 8:
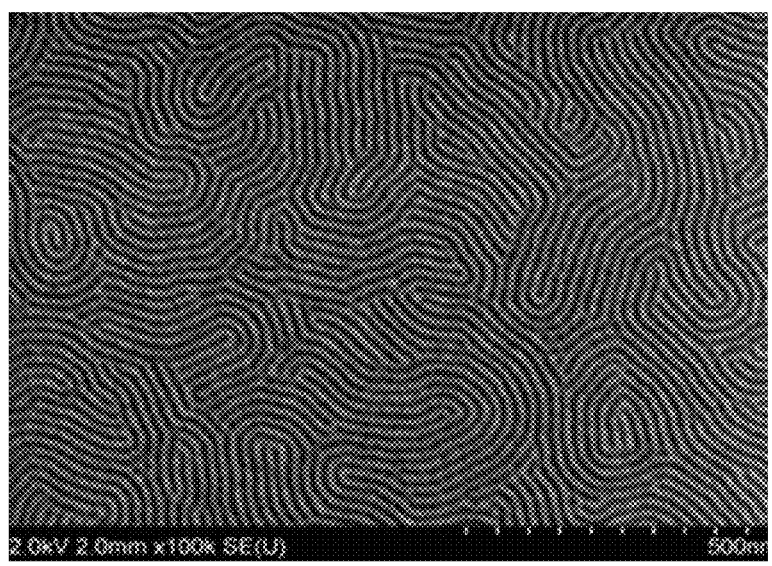

FIG. 7 shows the result of the GISAXS (Grazing Incident Small Angle X ray Scattering) analysis of the block copolymer of Example 1 performed with respect to the hydrophilic surface of which a contact angle at the room temperature with respect to the purified water was about 5 degrees, and FIG. 8 shows the result of the GISAXS (Grazing Incident Small Angle X ray Scattering) analysis of the block copolymer of Example 1 performed with respect to the hydrophobic surface of which a contact angle at the room temperature with respect to the purified water was about 60 degrees. From FIGS. 7 and 8, it can be confirmed that the in-plane phase diffraction patterns are observed in any case. From the above, it can be confirmed that the block copolymer can show the vertical aligning properties with respect to various substrates.

Figure 9:
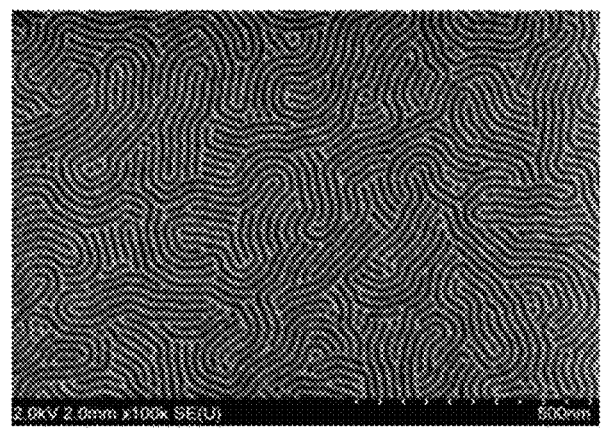
FIGS. 9 to 11 show SEM images of polymer layers.
Figure 10:
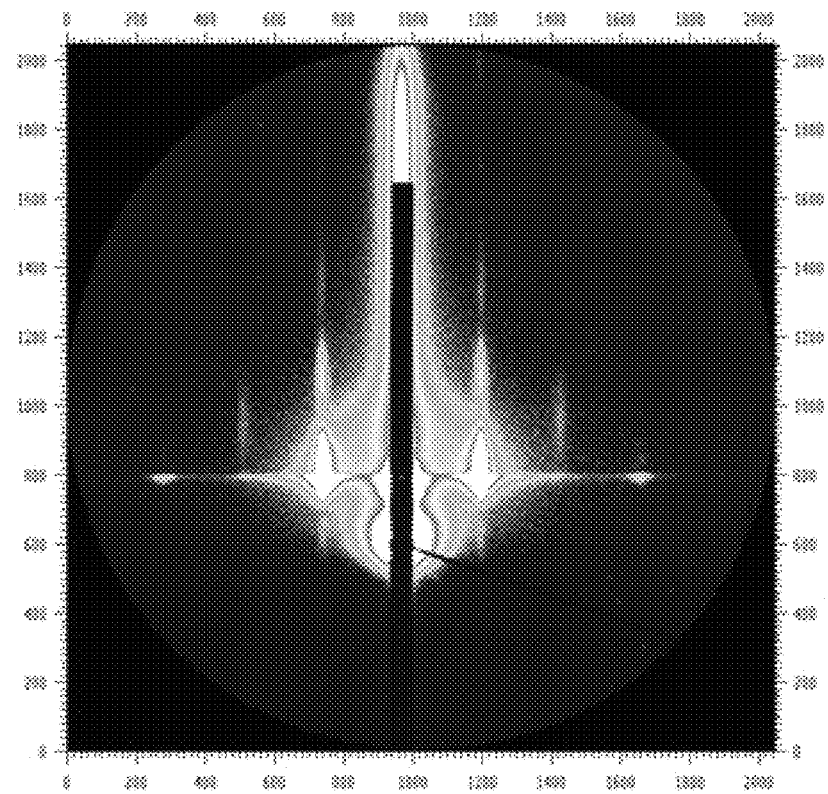
Figure 11:
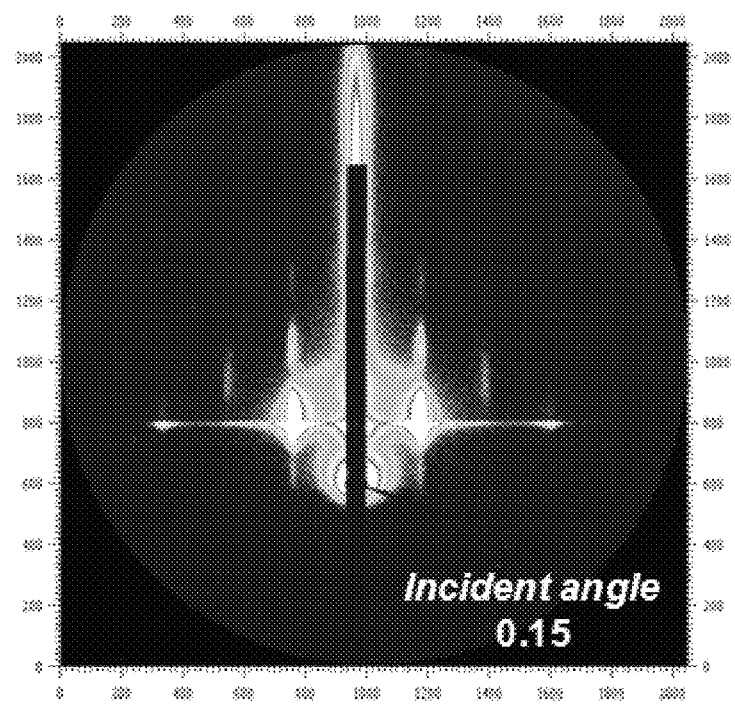

Further, by using the block copolymer of Example 1, polymer layers were formed by the same method as described above. The polymer layers were formed on a silicone substrate that was treated with the piranha solution that had a contact angle of 5 degrees of the purified water at the room temperature, a silicone oxide substrate that had a contact angle of 45 degrees of the purified water at the room temperature and a HMDS (hexamethyldisilazane) treated silicone substrate that had a contact angle of 60 degrees of the purified water at the room temperature, respectively. FIGS. 9 to 11 are the SEM images regarding the polymer layers on the surface having the contact angles of 5 degrees, 45 degrees and 60 degrees, respectively. From the Figures, it can be confirmed that the block copolymer forms the phase separation structure irrespective of surface properties of substrates.

TEST EXAMPLE 3

Properties Measurement of Block Copolymers

The results of evaluations regarding each block copolymer measured as above method are stated in the below Table.

TABLE 3

|  |  | Exs. | | | | | Com. Exs. | | | |
| --- | --- | --- | --- | --- | --- | --- | --- | --- | --- | --- |
|  |  | 1 | 2 | 3 | 4 | 5 | 1 | 2 | 3 | Ref. |
| The first | SE | 30.83 | 31.46 | 27.38 | 26.924 | 27.79 | 37.37 | 48.95 | 19.1 | 38.3 |
|  | De | 1 | 1.04 | 1.02 | 0.99 | 1.00 | 1.11 | 1.19 | 0.93 | 1.05 |

TABLE 3-continued

| | | Exs. | | | | | Com. Exs. | | | Ref. |
|---|---|---|---|---|---|---|---|---|---|---|
| | | 1 | 2 | 3 | 4 | 5 | 1 | 2 | 3 | |
| Block | VF | 0.66 | 0.57 | 0.60 | 0.61 | 0.61 | 0.73 | 0.69 | 0.76 | — |
| The | SE | 24.4 | 24.4 | 24.4 | 24.4 | 24.4 | 24.4 | 24.4 | 24.4 | 41.8 |
| Second | De | 1.57 | 1.57 | 1.57 | 1.57 | 1.57 | 1.57 | 1.57 | 1.57 | 1.18 |
| Block | VF | 0.34 | 0.43 | 0.40 | 0.39 | 0.39 | 0.27 | 0.31 | 0.24 | — |
| Difference of SE | | 6.43 | 7.06 | 2.98 | 2.524 | 3.39 | 12.98 | 24.55 | 5.3 | 3.5 |
| Difference of De | | 0.57 | 0.53 | 0.55 | 0.58 | 0.57 | 0.46 | 0.38 | 0.64 | 0.13 |
| Chain-forming atoms | | 12 | 8 | 10 | 14 | 16 | 4 | 1 | 12 | — |
| n/D | | 3.75 | 3.08 | 3.45 | 4.24 | 4.44 | 2.82 | 1.98 | — | — |

SE: surface energy (unit: mN/m)
De: density (unit: g/cm$^3$)
VF: volume fraction
Difference of SE: the absolute value of the difference between the surface energies of the first and the second block
Difference of De: the absolute value of the difference between the densities of the first and the second block
Chain-forming atoms: the number of the chain-forming atoms in the first block
Interval: interval (unit: nm) between the first blocks in the self assembled block copolymer
n/D: the number of the chain-forming atoms in the first block/Interval between the first blocks in the self assembled block copolymer
Ref.: Polystyrene-polymethylmethacrylate block copolymer (the first block: polystyrene block, the second block: polymethylmethacrylate block)

TEST EXAMPLE 4

Further, block copolymers having different volume fractions were prepared according to the same method as in Example 1, except that the molar ratios of the monomers and the macroinitiators were controlled.

The volume fractions are as below.

TABLE 4

| | Volume fraction of the first block | Volume fraction of the second block |
|---|---|---|
| Sample 1 | 0.7 | 0.3 |
| Sample 2 | 0.59 | 0.41 |
| Sample 3 | 0.48 | 0.52 |

The volume fraction of each block of the block copolymer was calculated based on a molecular weight measured by a GPC (Gel Permeation Chromatograph) and the density at the room temperature. In the above, the density was measured by the buoyancy method, specifically, was calculated by a mass in solvent (ethanol), of which a mass and a density in the air are known, and the GPC was performed according to the above described method.

Figure 12:
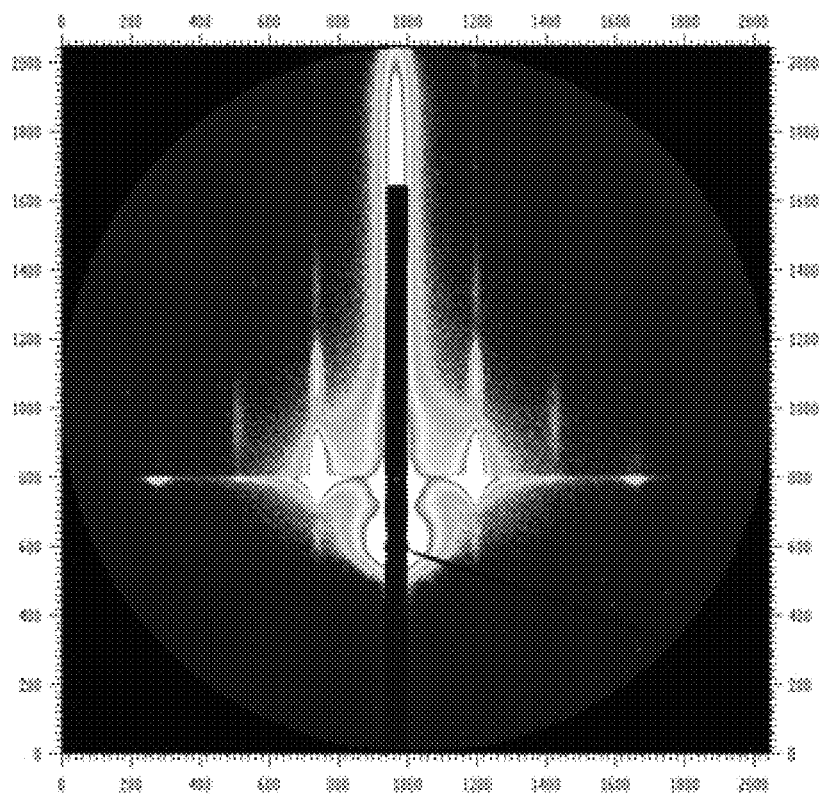
FIGS. 12 to 14 show GISAXS diffraction pattern.
Figure 13:
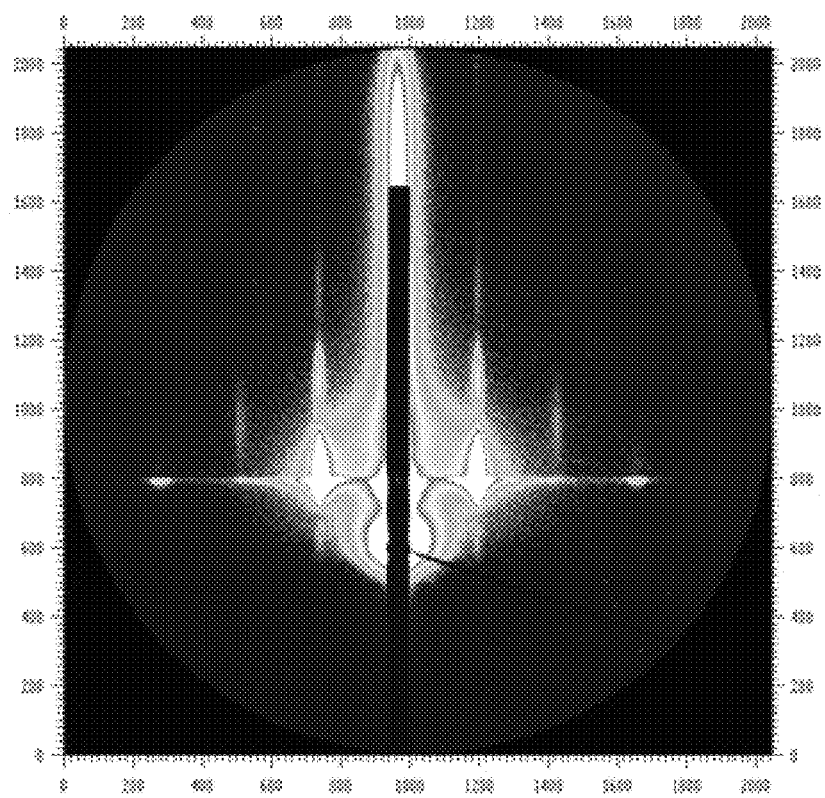
Figure 14:
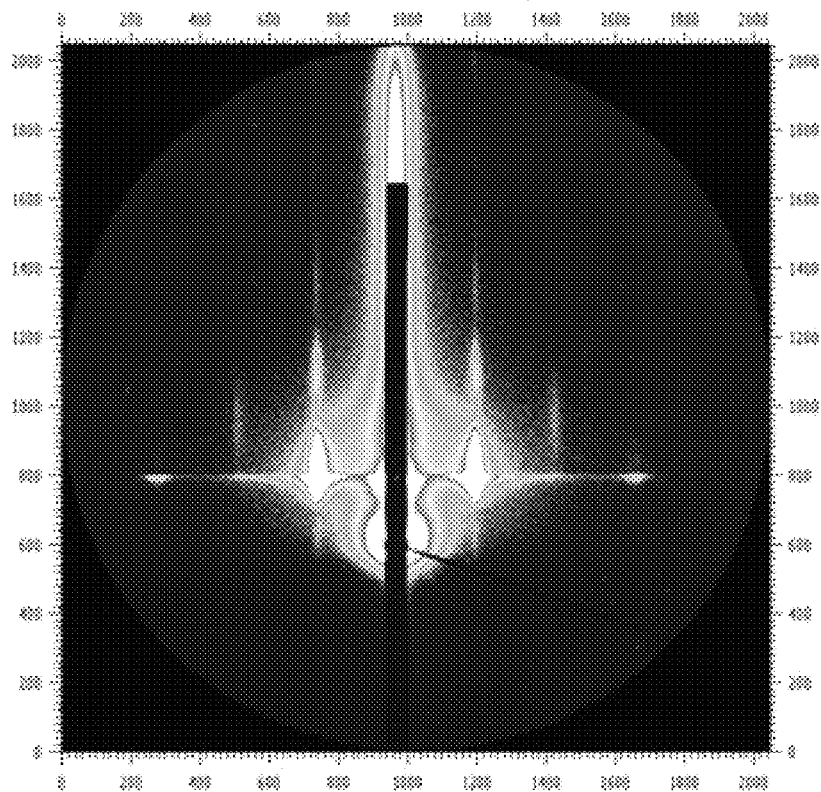

The polymer layer was obtained by spin coating a coating solution prepared by dissolving the block copolymer of each sample in fluorobenzene to a solid content of about 0.7 weight % on a silicone wafer so as for a coated thickness to be 5 nm (a coated area: a width=1.5 cm, a length=1.5 cm), and drying it for 1 hour at the room temperature and then subjecting it to a thermal annealing for 1 hour at about 160° C. Then, the GISAXS was performed and the results are illustrated in Figures. FIGS. 12 to 14 are the results of the samples 1 to 3, respectively, and it can be confirmed that the in-plane phase diffraction pattern is observed and the block copolymer has the vertical aligning property.

What is claimed is:

1. A block copolymer that comprises a first block and a second block different from the first block and that exhibits, in a X ray diffraction, at least one peak of which a full width at half maximum is from 0.2 nm$^{-1}$ to 1.5 nm$^{-1}$ at a range of scattering vector (q) from 0.5 nm$^{-1}$ to 10 nm$^{-1}$, wherein the first block comprises an aromatic structure to which a side chain having 10 or more chain-forming atoms is linked via a linker that is an oxygen atom, a sulfur atom, —NR$_1$—, —S(=O)$_2$—, an alkenylene group, an alkynylene group, or —X$_1$—C(=O)—, and directly connects an aromatic ring carbon of the aromatic structure to the side chain, wherein the R$_1$ is hydrogen, an alkyl group, an alkenyl group, an alkynyl group, an alkoxy group or an aryl group and the X$_1$ is an oxygen atom, a sulfur atom, —NR$_2$—, —S(=O)$_2$—, an alkylene group, an alkenylene group or alkynylene group, and the R$_2$ is hydrogen, an alkyl group, an alkenyl group, an alkynyl group, an alkoxy group or an aryl group, and wherein the X$_1$ in the —X$_1$—C(=O)— is attached to the aromatic structure, and the carbon atom in the —C(=O)— is attached to the side chain, and wherein the aromatic structure is linked to a main chain of the first block via a linker that is an oxygen atom, a sulfur atom, —S(=O)$_2$—, a carbonyl group, an alkylene group, an alkenylene group, an alkynylene group, —C(=O)—X$_2$— or —X$_2$—C(=O)—, and wherein the X$_2$ is a single bond, an oxygen atom, a sulfur atom, —S(=O)$_2$—, an alkylene group, an alkenylene group or alkynylene group.

2. The block copolymer according to claim 1, wherein the range of the scattering vector (g), within which the peak of which the full width at half maximum is from 0.2 nm$^{-1}$ to 1.5 nm$^{-1}$ is exhibited in the X ray diffraction is from 1 nm$^{-1}$ to 3 nm$^{-1}$.

3. The block copolymer according to claim 1, wherein the full width at half maximum of the peak exhibited in the range of the scattering vector (g) from 0.5 nm$^{-1}$ to 10 nm$^{-1}$ in the X ray diffraction is from 0.3 nm$^{-1}$ to 0.9 nm$^{-1}$.

4. The block copolymer according to claim 1, wherein the second block comprises an aromatic structure.

5. The block copolymer according to claim 4, wherein the aromatic structure of the second block comprises at least one halogen atom.

6. The block copolymer according to claim 5, wherein the halogen atom is a fluorine atom.

7. The block copolymer according to claim 1, wherein the aromatic structure of the first block does not have a halogen atom and the second block comprises an aromatic structure that has the halogen atom.

8. The block copolymer according to claim 1, wherein the first block is represented by Formula 1 below:

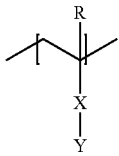

[Formula 1]

wherein the R is hydrogen or an alkyl group having 1 to 4 carbon atom(s), the X is an oxygen atom, a sulfur atom, $-S(=O)_2-$, a carbonyl group, an alkylene group, an alkenylene group, an alkynylene group, $-C(=O)-X_2-$ or $-X_2-C(=O)-$, where the $X_2$ is an oxygen atom, a sulfur atom, $-S(=O)_2-$, an alkylene group, an alkenylene group or an alkynylene group and the Y is a monovalent substituent comprising the aromatic structure to which the chain having 10 or more chain-forming atoms is linked.

9. The block copolymer according to claim 1, wherein the second block is represented by Formula 3 below:

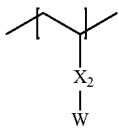

[Formula 8]

wherein the $X_2$ is a single bond, an oxygen atom, a sulfur atom, $-S(=O)_2-$, an alkylene group, an alkenylene group, an alkynylene group, $-C(=O)-X_1-$ or $-X_1-C(=O)-$, where the $X_1$ is a single bond, an oxygen atom, a sulfur atom, $-S(=O)_2-$, an alkylene group, an alkenylene group or an alkynylene group, and the W is an aryl group comprising at least one halogen atom.

10. The block copolymer according to claim 1, wherein it is capable of forming a layer exhibiting an in-plane phase diffraction pattern in a grazing incidence small angle X ray scattering.

11. The block copolymer according to claim 1, wherein its number average molecular weight is from 3,000 to 300,000.

12. The block copolymer according to claim 1, wherein its polydispersity (Mw/Mn) is from 1.01 to 1.60.

13. A polymer layer comprising a self assembled product of the block copolymer of claim 1.

14. The polymer layer according to claim 13, wherein it exhibits an in-plane phase diffraction pattern in a grazing incidence small angle X ray scattering.

15. A method for forming a polymer layer, comprising forming the polymer layer comprising a self assembled product of the block copolymer of claim 1.

16. A pattern-forming method comprising selectively removing the first block or the second block of the block copolymer from a laminate comprising a substrate and a polymer layer that is formed on the substrate and that comprises a self-assembled product of the block copolymer of claim 1.

* * * * *